(12) United States Patent
Freeman et al.

(10) Patent No.: US 8,128,589 B2
(45) Date of Patent: Mar. 6, 2012

(54) APPARATUS AND METHODS FOR ENZYMATIC DEBRIDEMENT OF SKIN LESIONS

(75) Inventors: Amihay Freeman, Ben Shemen (IL); Eran Hirszowicz, Ramat-Gan (IL); Michal Be'eri-Lipperman, Moshav Beit Heruth (IL)

(73) Assignees: Ramot at Tel-Aviv University Ltd., Tel-Aviv (IL); EnzySurge Ltd., Rosh HaAyin (IL)

( * ) Notice: Subject to any disclaimer, the term of this patent is extended or adjusted under 35 U.S.C. 154(b) by 1568 days.

(21) Appl. No.: 11/493,381

(22) Filed: Jul. 25, 2006

(65) Prior Publication Data

US 2007/0041960 A1   Feb. 22, 2007

Related U.S. Application Data

(63) Continuation of application No. PCT/IL2005/000101, filed on Jan. 27, 2005, which is a continuation-in-part of application No. 10/768,749, filed on Jan. 27, 2004, now Pat. No. 7,364,565.

(51) Int. Cl.
*A61N 1/30* (2006.01)
(52) U.S. Cl. ........................................... 604/19
(58) Field of Classification Search .............. 604/27, 604/43, 93, 174, 175, 506, 96.01, 104, 164.1, 604/913, 19; 600/367, 362, 573, 579, 363, 600/576; 606/201, 202
See application file for complete search history.

(56) References Cited

U.S. PATENT DOCUMENTS

| | | | |
|---|---|---|---|
| 191,775 A | 6/1877 | Parsons | 604/40 |
| 551,973 A | 12/1895 | Knap | 604/40 |
| 1,138,346 A | 5/1915 | Bacon | 122/114 |
| 1,178,898 A | 4/1916 | Young | 604/42 |
| 1,385,346 A | 7/1921 | Herbert et al. | |
| 2,884,389 A | 4/1959 | Corwin et al. | |
| 3,288,140 A | 11/1966 | McCarthy | 604/289 |
| 3,556,097 A | 1/1971 | Wallace | 128/202.23 |
| 3,910,266 A | 10/1975 | Kawase | 128/66 |
| 4,105,783 A | 8/1978 | Yu et al. | 424/283 |
| 4,122,158 A | 10/1978 | Schmitt | 424/27 |
| 4,197,291 A | 4/1980 | Klein et al. | 424/94 |
| 4,226,854 A | 10/1980 | Klein et al. | 424/94 |
| 4,307,081 A | 12/1981 | Klien et al. | 424/94 |

(Continued)

FOREIGN PATENT DOCUMENTS

CN   1929883   3/2007

(Continued)

OTHER PUBLICATIONS

GB 2378392, UK Patent Application, Stonier, date of publication: Dec. 2, 2003.*

(Continued)

*Primary Examiner* — Manuel A Mendez

(57) ABSTRACT

An apparatus for debridement of devitalized tissue in skin lesions, that includes a plurality of height- and angle-adjustable inlet tubes and at least one outlet tube and a member that forms an occlusive seal around a skin lesion. The plurality of inlet tubes is adapted for directing a continuous stream of enzymatic solution to the surface and into the entire volume of the wound bed of the lesion and the at least one outlet is adapted for removing the enzymatic solution, fluids draining from the lesion and tissue debris from the occluded skin lesion.

26 Claims, 16 Drawing Sheets

U.S. PATENT DOCUMENTS

| | | | |
|---|---|---|---|
| 4,329,430 A | 5/1982 | Klein et al. | 424/94 |
| 4,363,815 A | 12/1982 | Yu et al. | 424/274 |
| 4,645,668 A | 2/1987 | Pinnell | 424/94 |
| 4,798,599 A | 1/1989 | Thomas | 604/290 |
| 4,969,881 A | 11/1990 | Viesturs | 604/305 |
| 5,037,431 A | 8/1991 | Summers et al. | 606/131 |
| 5,106,621 A | 4/1992 | Rowan et al. | 424/94.65 |
| 5,156,846 A | 10/1992 | Petersen et al. | 424/443 |
| 5,242,392 A | 9/1993 | Vaughn | 604/80 |
| 5,330,498 A * | 7/1994 | Hill | 606/194 |
| 5,358,494 A | 10/1994 | Svedman | 604/313 |
| 5,409,546 A | 4/1995 | Nakagawa et al. | 134/42 |
| 5,441,482 A | 8/1995 | Clague et al. | 604/35 |
| 5,480,410 A * | 1/1996 | Cuschieri et al. | 606/213 |
| 5,520,727 A | 5/1996 | Vreeland et al. | |
| 5,523,092 A * | 6/1996 | Hanson et al. | 424/423 |
| 5,695,457 A * | 12/1997 | St. Goar et al. | 604/4.01 |
| 5,697,920 A | 12/1997 | Gibbons | 604/289 |
| 5,735,833 A | 4/1998 | Olson | 604/289 |
| 5,830,739 A | 11/1998 | Houck et al. | 435/219 |
| 5,898,211 A | 4/1999 | Marshall et al. | 257/601 |
| 5,941,859 A | 8/1999 | Lerman | 604/289 |
| 5,958,406 A | 9/1999 | de Faire et al. | 424/94.63 |
| 5,976,556 A | 11/1999 | Norton et al. | 424/401 |
| 5,989,211 A | 11/1999 | Schaumann et al. | 604/27 |
| 6,008,040 A | 12/1999 | Datar | 435/325 |
| 6,017,531 A | 1/2000 | Fortney et al. | 424/94.63 |
| 6,045,570 A | 4/2000 | Epstein et al. | 606/214 |
| 6,117,433 A | 9/2000 | Edens et al. | 424/400 |
| 6,135,116 A | 10/2000 | Vogel et al. | 128/898 |
| 6,146,626 A | 11/2000 | Markert et al. | 424/94.63 |
| 6,261,275 B1 | 7/2001 | Hayes | 604/294 |
| 6,264,666 B1 | 7/2001 | Coleman et al. | 606/131 |
| 6,293,929 B1 * | 9/2001 | Smith et al. | 604/289 |
| 6,368,595 B2 | 4/2002 | Edens et al. | 424/94.6 |
| 6,398,767 B1 | 6/2002 | Fleischmann | 604/313 |
| 6,406,447 B1 | 6/2002 | Thrash et al. | 601/160 |
| 6,416,626 B1 | 7/2002 | Park et al. | 162/168.1 |
| 6,458,109 B1 | 10/2002 | Henley et al. | 604/304 |
| 6,520,982 B1 | 2/2003 | Boynton | 607/104 |
| 6,695,823 B1 | 2/2004 | Lina et al. | 604/304 |
| 6,767,334 B1 | 7/2004 | Randolph | 604/5 |
| 6,856,821 B2 | 2/2005 | Johnson | 600/1 |
| 6,892,405 B1 | 5/2005 | Dimitriu et al. | 5/615 |
| 6,904,631 B2 | 6/2005 | Vrzalik et al. | 5/615 |
| 6,936,037 B2 | 8/2005 | Bubb et al. | 604/327 |
| 6,942,649 B2 | 9/2005 | Ignon et al. | 604/289 |
| 6,945,955 B1 * | 9/2005 | Michel et al. | 604/93.01 |
| 6,951,553 B2 | 10/2005 | Bubb et al. | 604/327 |
| 6,994,702 B1 | 2/2006 | Johnson | 606/9 |
| 7,004,915 B2 | 2/2006 | Boynton et al. | 601/6 |
| 2002/0115952 A1 | 8/2002 | Johnson | 600/1 |
| 2002/0143286 A1 | 10/2002 | Tumey | 604/11 |
| 2003/0021775 A1 * | 1/2003 | Freeman | 424/94.6 |
| 2003/0040687 A1 | 2/2003 | Boynton et al. | 601/6 |
| 2003/0050594 A1 | 3/2003 | Zamierowshi | 604/46 |
| 2003/0219469 A1 | 11/2003 | Johnson et al. | 424/445 |
| 2003/0225441 A1 | 12/2003 | Boynton et al. | 607/104 |
| 2004/0039415 A1 | 2/2004 | Zamierowski | 606/215 |
| 2004/0186421 A1 | 9/2004 | Freeman | |
| 2005/0182445 A1 | 8/2005 | Zamierowski | 606/213 |
| 2005/0229321 A1 | 10/2005 | Phillips et al. | 5/715 |
| 2005/0234510 A1 | 10/2005 | Zamierowski | 606/215 |
| 2005/0240220 A1 | 10/2005 | Zamierowski | 606/215 |
| 2006/0029675 A1 | 2/2006 | Ginther | 424/486 |
| 2007/0057699 A1 | 3/2007 | Tumer et al. | |

FOREIGN PATENT DOCUMENTS

| | | | |
|---|---|---|---|
| EP | 0355186 A | | 2/1990 |
| EP | 1014905 | | 7/2000 |
| EP | 1284777 B1 | | 2/2003 |
| EP | 1418973 A2 | | 5/2004 |
| EP | 1443988 | | 8/2004 |
| GB | 641061 A | | 8/1950 |
| GB | 2378392 A | | 2/2003 |
| JP | 2001-514041 | | 9/2001 |
| JP | 2003-520072 | | 7/2003 |
| WO | WO 99/11192 | | 3/1999 |
| WO | WO 01/37922 | | 5/2001 |
| WO | WO 03/001136 A1 | | 1/2003 |
| WO | WO 03/011369 A1 | | 2/2003 |
| WO | WO 03/23783 | | 3/2003 |
| WO | WO 2006/092798 | | 9/2006 |

OTHER PUBLICATIONS

Communication Pursuant to Article 94(3) EPC Dated Jul. 13, 2009 From the European Patent Office Re.: Application No. 05703144.5.

Office Action Dated Nov. 14, 2008 From the State Intellectual Property Office of the People's Republic of China Re.: Appliction No. 200580008053.7.

Office Action Dated Oct. 23, 2006 From the Israeli Patent Office Re.: Application No. 160090.

International Search Report Dated Nov. 20, 2002 From the International Searching Authority Re.: Application No. PCT/IL02/00572.

Office Action Dated Feb. 7, 2010 From the Israel Patent Office Re.: Application No. 176972 and Its Translation Into English.

Response Dated Jan. 4, 2010 to Office Action of Jun. 4, 2009 From the Israeli Patent Office Re.: Application No. 176972.

Response Dated Jan. 17, 2010 to Communication Pursuant to Article 94(3) EPC of Jul. 13, 2009 From the European Patent Office Re.: Application No. 05703144.5.

Response Dated Jun. 7, 2010 to Office Action of Feb. 7, 2010 From the Israel Patent Office Re.: Application No. 176972.

Translation of Official Action Dated May 21, 2010 From the Japanese Patent Office Re. Application No. 2006-550490.

Response Dated Sep. 16, 2010 to Official Action of May 21, 2010 From the Japanese Patent Office Re. Application No. 2006-550490.

Freeman, A., "Streaming of Proteolytic Enzyme Solutions for Wound Debridement: A Feasibility Study", Wounds, vol. 16(6), pp. 201-205 (2004).

Rodeheaver, G., "Proteolytic Enzymes As Adjuncts to Antimicrobial Prophylaxis of Contaminated Wounds", Am J Surg., vol. 129(5), pp. 537-544 (1975).

Falanga, V., "Wound Bed Preparation and the Role of Enzymes: A Case for Multiple Action of Therapeutic Agents", Wounds, vol. 14(2), pp. 47-57 (2002).

Official Action Dated Apr. 19, 2005 From the US Patent and Trademark Office Re.: U.S. Appl. No. 10/768,749.

Office Action Dated Jun. 4, 2009 From the Israeli Patent Office Re.: Application No. 176972 and Its Translation Into English.

U. Rutishauser et al., "Immunological Function of Lymphocytes Fractionated with Antigen-Derivatized Fibers," Proc. Nat. Acad. Sci. USA, 70(12): 3894-3898 (1973).

H. Wigzell et al., "Cell separation on antigen-coated columns: elimination of high rate antibody-forming cells and immunological memory cells," J. Exp. Med. 129: 23-36 (1969).

L.J. Wysocki et al., "Panning for lymphocytes: a method for cell selection," Proc. Natl. Acad. Sci. USA 75(6): 2844-2848 (1978).

Supplementary Response Dated Oct. 26, 2010 to Official Action of May 21, 2010 From the Japanese Patent Office Re. Application No. 2006-550490.

Translation of Official Action Dated Mar. 8, 2011 From the Japanese Patent Office Re. Application No. 2006-550490.

* cited by examiner

 
Figure 16A　　　　　　　　　　　Figure 16B
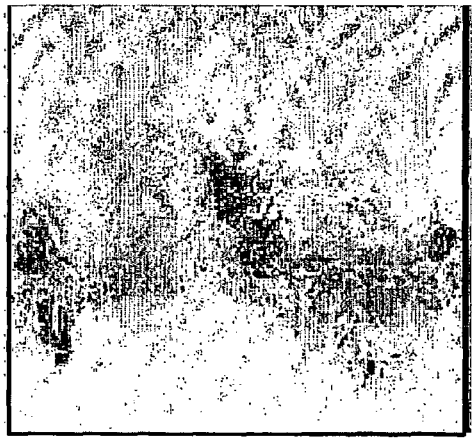 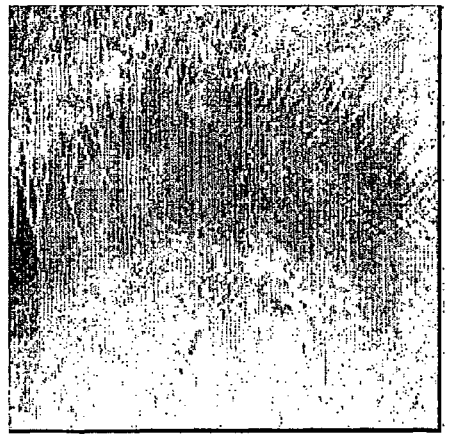
Figure 17A　　　　　　　　　　　Figure 17B

APPARATUS AND METHODS FOR ENZYMATIC DEBRIDEMENT OF SKIN LESIONS

CROSS-REFERENCE TO RELATED APPLICATIONS

This application is a continuation of International application PCT/IL2005/000101 filed Jan. 27, 2005, which is a continuation-in-part of application Ser. No. 10/768,749 filed Jan. 27, 2004 now U.S. Pat. No. 7,364,565. The entire content of each prior application is expressly incorporated herein by reference thereto.

FIELD OF THE INVENTION

The present invention relates to apparatus and methods for debridement of devitalized tissue in skin lesions, the apparatus comprising a plurality of height-and angle-adjustable inlet tubes, at least one outlet tube and means to form an occlusive seal around a skin lesion.

BACKGROUND OF THE INVENTION

Acute and chronic diseases, such as diabetes and psoriasis, or acute injuries result in a severe damage to the skin. This damage may involve the entire thickness of the skin and may often include deeper tissues wherein the depth of the damage varies over the entire damaged zone. The damaged skin loses the anatomic organization of a healthy skin as the stratum corneum is at least partially destroyed and consequently the inner layers of the skin are no longer protected from the external environment. Moreover, the damaged skin typically contains dead eschar, diseased and/or abnormal cells that must be removed in order to enable healing. Leaving the dead eschar in place extends and deepens the damage into the neighboring, undamaged tissues. This dead eschar also serves as a medium for bacteria growth, and a source of infection, contamination and sepsis which may be life threatening.

Removal of the dead eschar, diseased and/or abnormal cells, also known as "debridement", is executed either by surgical procedures or by using enzymatic means. Surgery is one of the most common procedures of debridement wherein small necrotic areas are excised of the entire damaged skin. This method is limited to small non-tangential surfaces. It also involves the removal of large fractions of healthy tissue which, if preserved, could serve as a source for the natural healing processes. Surgical procedures are also long, expensive and require complicated medical resources.

U.S. Pat. No. 3,910,266 describes a method and apparatus that provide a jet of pressurized fluids which is used for penetrating the skin and inserting cosmetic or therapeutic agents into the skin. U.S. Pat. No. 5,697,920 describes means for mechanic debriding using a jet of pressurized fluids and a brush. U.S. Pat. Nos. 5,941,859; 5,989,211 and 6,264,666 describe medical instruments for supplying to and removing rinsing fluids from the skin. A hand-held surgical apparatus adapted to be used substantially as a sharp surgical tool for removal of diseased tissue by utilizing pressurized fluid jets, is described in U.S. Pat. Nos. 5,037,431. 5,358,494 describes an irrigation dressing comprising a conduit for supplying the irrigation fluids and pad attached at the tip of the conduit wherein the pad is adapted to fill the wound cavity, thereby supporting the walls of the wound. However, the methods and apparatus described in the above patents are not adapted for providing a sealed system that occludes a defined treatment zone. Furthermore, these methods and apparatus cannot provide a sealed environment that encompasses the wound and that is resistant to pressure accumulated therein.

U.S. Pat. No. 4,969,881 describes a hyperbaric oxygen dressing adapted for treating body sores with a flow of oxygen by supplying oxygen through a suitable feed tube dressing utilizing a gas releasing system. The dressing described in this patent is not suitable for draining secretions or excess therapeutic materials from the wound area and/or for providing a flow of therapeutic solution to the wound area.

U.S. Patent Application, Publication No. 2003/0050594, describes a wound therapy system adapted for treating a wound with a gradient of various mechanical forces, particularly vacuum, the system comprising transfer assembly, collecting assembly and a source for establishing said gradient, specifically a pump, connected to the transfer assembly. U.S. Patent Application, Publication No. 2003/0225441, describes a device for applying thermotherapeutic liquids to a selected area of a patient, the device comprising an applicator for maintaining liquids at a desired temperature, the applicator being held about the selected area through negative pressure generated by a pump connected thereto.

U.S. Pat. No. 6,135,116 describes a method for wound therapy, comprising providing pneumatic compression therapy and vacuum assisted closure therapy, concurrently. U.S. Pat. No. 6,767,334 describes a wound treatment device adapted to provide a positive pressure to a wound site, the device comprises a pad for inserting into the wound, a pump and a fluid conduit for conveying fluids through the pad to the wound, a venturi communication to create suction at the pad and within the wound cavity and a reservoir for collecting the fluid from the wound U.S. Pat. Nos. 1,385,346; 6,398,767; 6,458,109 and EP 1014905 describe dressings which are secured to the skin surface around a wound. Each dressing includes a single infusion tube and a single drainage tube having a fixed position with respect to the wound surface. International Patent Application, Publication No. WO 03/01136, assigned to the common assignees of the present invention, describes a device for the removal of cells from a viable tissue. The device includes an inlet tube adapted for applying a stream of enzymatic solutions over and onto the tissue and an outlet tube for removing excess fluids and debris. The distance between the opening of the outlet tube and the skin may be adjusted by a screw mechanism. Each one of the dressing and devices described in the aforementioned inventions include a single infusion (inlet) tube having a fixed position with respect to the wound. Thus, these dressing and devices cannot be adjusted to penetrate deeply into the lesion and are unsuitable for infusing areas that are not readily accessible.

A paper by the inventor of the present invention published after the priority date of the present application describes applying a stream of active proteolytic enzyme for a few hours to provide an effective debridement (Freeman et al., Wound 16:201-205, June 2004). The streaming of a buffer solution devoid of enzymes was found to be ineffective. Furthermore, treatment with static enzyme solution for a similar time period had no effect and visual change was not observed.

Enzymatic debridement is advantageous over mechanical and surgical debridement mainly since it is less painful and does not involve the loss of a great deal of blood. The application of proteolytic enzymes for debridement is well known in the art (G. Rodeheaver, 1975, Am. J. Surg. 129(5):537-544). These enzymes include those generally found in to plant sources, such as papaya (papain), fig (ficin), and pineapple (bromelain). Hydrolytic enzymes derived from the pineapple plant that are useful for digestion, dissection and separation of non-viable, especially eschar tissue, from viable tissue in a mammalian host are described in U.S. Pat. Nos. 4,197,291; 4,226,854; 4,307,081; 4,329,430 and 5,830,739 among others. U.S. Pat. No. 6,017,531 describes a proteolytic composition which includes an extracellular neutral protease produced by *Vibrio proteolyticus*.

The degree of therapeutic activity obtained from topical application of proteolytic enzymes is governed, inter alia, by the intrinsic catalytic characteristics of those enzymes. The major problems associated with topical use of compositions comprising proteolytic enzymes are that the catalytic activity of the enzymes rapidly attenuates due to the typical low pH at the lesion area, adsorption of enzyme molecules to the surface of the wound bed and/or the surface of the dressing thus preventing their accessibility to other regions at the wound bed and inhibition of enzymatic activity by moieties within the wound exudates. Accordingly, obtaining stable enzymatic formulations is often complicated.

SUMMARY OF THE INVENTION

The present invention relates to apparatus and methods for debriding the devitalized tissue of skin lesions. The apparatus of the present invention overcomes the drawbacks of the background art by providing a continuous flow of therapeutic solutions into the wound bed of the skin lesion, through a plurality of adjustable inlet tubes. In an embodiment of the present invention, the therapeutic solutions may include catalytically active proteolytic enzymes.

It is to be understood that the terms "skin lesion" and "lesion" as used herein are to be construed according to their broadest meaning, to describe damaged skin comprising devitalized tissue, including but not limited to, chronic cutaneous ulcers (e.g. diabetic ulcers and decubitus ulcers) and burns. The skin lesion may extend through all or through part of the skin layers and may further extend through the underlying muscles and tissues.

The method and apparatus of the present invention provide efficient debridement of devitalized tissue without the necessity of any surgical intervention. The apparatus of the invention is advantageous over other non-surgical debriding means known in the art since it is configured to continuously supply therapeutic solutions, particularly solutions comprising catalytically active debriding enzymes, to any desired depth and at any angle. Hence, the present invention is suitable for treatment of a variety of lesions, including deep skin lesions such as Stage II and Stage III lesions. The apparatus may be further adapted to generate and maintain positive or negative pressure at the site of the lesion, which as detailed above, are known to enhance healing. Thus, the apparatus of the invention may be adapted for a combined therapy encompassing enzymatic debridement with negative/positive pressure.

In an embodiment of the present invention, there is provided an applicator for treating a skin lesion, said applicator comprising:
  (a) a housing unit having at least one aperture formed therein; and
  (b) means for affixing the applicator to the skin around the circumference of skin lesion;
  wherein said housing unit comprising:
    (i) a plurality of inlet tubes, each of said plurality of inlet tubes having a first longitudinal axis and configured to be adjustable along its longitudinal axis through said at least one aperture; and
    (ii) at least one outlet tube having a second longitudinal axis.

According to one embodiment, the housing unit comprises a plurality of apertures, wherein each of said plurality of inlet tubes and the at least one outlet tube extend through a corresponding one of each of said plurality of apertures.

According to yet another embodiment, said at least one outlet tube is configured to be adjustable through its corresponding aperture.

According to another embodiment, the applicator further comprises a plurality of sealing units, each sealing unit being configured to prevent the passage of fluids between the external diameter of each inlet tube and its corresponding aperture. According to another embodiment, the apparatus further comprises at least one sealing unit being configured to prevent the passage of fluids between the external diameter of said at least one outlet tube and its corresponding aperture.

According to another embodiment, each of said plurality of inlet tubes has a proximal end and a distal end, said distal end configured to face said skin lesion. According to yet another embodiment, each of said plurality of inlet tubes is adjustable in position and angle with respect to the housing unit. According to yet another embodiment the distal end of each of said plurality of inlet tubes is smoothly curved to form a non-traumatic tip. According to yet another embodiment, the opening at the distal end of at least one inlet tube is at an angle with respect to the central axis of the inlet tube. According to yet another embodiment, the distal end comprises a plurality of openings.

According to a preferred embodiment, each inlet tube is transparent. According to yet another preferred embodiment, each inlet tube is made of a flexible elastomer. According to yet another embodiment, the flexible elastomer comprises a material selected from the group consisting of: silicone, polyurethane, natural rubber, neoprene and ethyl vinyl acetate.

According to yet another embodiment, each inlet tube is extendable or retractable along its longitudinal axis. According to yet another embodiment, the applicator further comprises an adjustable screw mechanism in communication with each of said inlet tubes thereby to extend or retract each inlet tube along its longitudinal axis.

According to yet another embodiment, the applicator further comprises at least one reservoir in fluid communication with the plurality of inlet tubes. According to yet another embodiment, the at least one reservoir is adapted for holding a therapeutic solution. According to yet another embodiment, the at least one reservoir is made of a material selected from the group consisting of: plastic, glass, steel and ceramics.

According to yet another embodiment, the applicator further comprises a connector being in fluid communication with at least one inlet tube and with the at least one reservoir, the connector is adapted for opening and closing the fluid communication between the at least one inlet tube and said at least one reservoir. According to yet another embodiment, the connector includes at least one element selected from the group consisting of: luer lock and valve means.

According to yet another embodiment, the applicator further comprises a separator being in fluid communication with at least one inlet tube and with the at least one reservoir, the separator is adapted for reversibly disconnecting and reconnecting the at least one inlet tube from said at least one reservoir.

According to yet another embodiment, the applicator further comprises a control means being in fluid communication with at least one inlet tube and with the at least one reservoir, the control means is adapted to control the flow rate of fluids flowing from the at least one reservoir through the at least one inlet tube. According to yet another embodiment, the control means is selected from the group consisting of: peristaltic pump and a drip counter.

According to yet another embodiment, the applicator further comprises a thermo-regulating means being in communication with the at least one reservoir, thereby to affect the temperature of fluids held in said at least one reservoir. According to another embodiment, the applicator further comprises a thermo-regulating means being in communication with at least one inlet tube of said plurality of inlet tubes, thereby to affect the temperature of fluids flowing through said at least one inlet tube.

According to yet another embodiment, the applicator further comprises at least one filter fitted within at least one inlet tube of said plurality of inlet tubes, for filtering fluids flowing within said at least one inlet tube.

According to yet another embodiment, the applicator further comprises a collecting reservoir being in fluid communication with the at least one outlet tube and configured to collect fluids draining from said at least one outlet tube.

According to another alternative embodiment, the applicator further comprises a plurality of reservoirs, wherein a first reservoir of said plurality of reservoirs being adapted for holding a first solution comprising at least one catalytically non-active protease and wherein a second reservoir of said plurality of reservoirs being adapted for holding a second solution comprising an agent capable of activating the at least one catalytically non-active protease, the first reservoir and the second reservoir being in fluid communication with one another and at least one of said first and second reservoirs further being in fluid communication with at least one inlet tube of said plurality of inlet tubes. According to an alternative embodiment, the applicator further comprises a mixing chamber being in fluid communication with said first and second reservoirs and with said at least one inlet tube, wherein the mixing chamber is adapted to hold a catalytically active proteolytic mixture comprising said first and second solutions. According to yet another embodiment, the mixing chamber further comprises mixing means.

According to yet another embodiment the applicator further comprises a vacuum source being in fluid communication with the at least one outlet tube, thereby generating a negative pressure at the occluded skin lesion.

According to a preferred embodiment the therapeutic solution comprises an effective amount of at least one catalytically active protease. According to yet another embodiment, the at least one catalytically active protease. According to yet another embodiment, the at least one catalytically active protease is selected from the group consisting of: papain, bromelain, plasminogen activator, plasmin, mast cell protease, lysosomal hydrolase, streptokinase, pepsin, vibriolysin, krill protease, chymotrypsin, trypsin, collagenase, elastase, dipase, proteinase K, *Clostridium* multifunctional protease and *Bacillus subtilis* protease.

According to yet another embodiment, the means for affixing the applicator to the skin comprises a first plane attached to the housing and a second plane configured to surround and adhere to the lesion. According to yet another embodiment, the adhesive means is transparent. According to yet another embodiment, the adhesive means is biocompatible. According to yet another embodiment, the second plane is covered with a protective detachable film.

According to yet another embodiment, at least one of said plurality of inlet tubes comprises a deflectable wire operatively linked thereto and extending along the first longitudinal axis of said at least one inlet tube. According to a preferred embodiment, said deflectable wire does not extend beyond said distal end of said at least one inlet. According to yet another embodiment, the deflectable wire comprises a rigid material that is flexible and elastic. According to yet another embodiment, the deflectable wire comprises a material selected from the group consisting of: silver, platinum, stainless steel and polymer. According to yet another embodiment, said at least one inlet tube comprises a first longitudinal lumen for holding fluids and a second longitudinal lumen configured to hold the deflectable wire.

In another embodiment of the present invention, there is provided an apparatus for treating a skin lesion, said apparatus comprising:
(a) a spacer for occluding an area comprising the skin lesion, the spacer having a lower plane facing the skin, an upper plane facing the housing, wherein the lower plane comprises adhesive means for affixing the spacer to the skin at the circumference of said skin lesion; and
(b) an applicator comprising a housing unit, said housing unit comprising:
 (i) a plurality of inlet tubes, each of said plurality of inlet tubes having a first longitudinal axis and configured to be adjustable along its longitudinal axis through said at least one aperture;
 (ii) at least one outlet tube having a second longitudinal axis; and
 (iii) means for affixing the applicator to the upper plane of the spacer.

According to one embodiment, the spacer comprises an elastomer. According to another embodiment, the elastomer is a foam-like material. According to yet another embodiment, the spacer comprises a material selected from the group consisting of: silicone, silicone foam, polyurethane, natural rubber, neoprene and ethyl vinyl acetate foam. According to yet another embodiment, the adhesive means for affixing the spacer to the skin comprising a material selected from the group consisting of: thermoplastic resin, pressure sensitive adhesive, hydrocolloid adhesive and rubber. According to another embodiment, the lower plane of the spacer is covered with a protective detachable film According to yet another embodiment, the spacer has a predetermined closed shape. According to yet another embodiment, the spacer has a continuous elongated shape that forms a closed shape in situ.

In yet another embodiment of the present invention, there is provided a method for treating a skin lesion, the method comprising:
(a) providing an applicator, said applicator comprising a housing unit having at least one aperture formed therein, and means for affixing the applicator to the skin around the circumference of the skin lesion, wherein said housing unit comprising:
 (i) a plurality of inlet tubes, each of said plurality of inlet tubes having a first longitudinal axis and configured to be adjustable along its longitudinal axis through said at least one aperture; and
 (ii) at least one outlet tube having a second longitudinal axis;
(b) placing against the skin at the circumference of said skin lesion said means, thereby affixing the apparatus to the skin at the circumference of said skin lesion to obtain an occluded lesion;
(c) connecting the plurality of inlet tubes to at least one reservoir by a fluid communication, wherein the at least one reservoir encompassing a debriding solution comprising at least one catalytically active protease;
(d) initiating a flow of the debriding solution from the at least one reservoir through at least one inlet tube of the plurality of inlet tubes to the occluded lesion; and
(e) draining said solution from said occluded lesion through the at least one outlet tube.

According to one embodiment, the method further comprises adjusting the position and angle of each of said plurality of inlet tubes with respect to said housing.

According to an alternative embodiment, the method comprises:
(a) providing an apparatus comprising an applicator, said applicator comprising a housing unit having at least one aperture formed therein, and means for affixing the applicator, wherein said housing unit comprising:
  (i) a plurality of inlet tubes, each of said plurality of inlet tubes having a first longitudinal axis and configured to be adjustable along its longitudinal axis through said at least one aperture; and
  (ii) at least one outlet tube having a second longitudinal axis;
(b) providing a spacer for occluding the skin lesion, the spacer having a lower plane facing the skin, an upper plane facing the housing of said applicator, wherein the lower plane comprises adhesive means for affixing the spacer to the skin at the circumference of said skin lesion;
(c) affixing the lower plane of the spacer to the skin at the circumference of said skin lesion;
(f) affixing the applicator to the upper plane of the spacer, thereby obtaining an occluded lesion;
(g) connecting the plurality of inlet tubes to at least one reservoir by a fluid communication, wherein the at least one reservoir encompassing a debriding solution comprising at least one catalytically active protease;
(h) initiating a flow of the debriding solution from the at least one reservoir through at least one inlet tube of the plurality of inlet tubes to the occluded lesion; and
(i) draining said solution from said occluded lesion through the at least one outlet tube.

According to yet another embodiment step (c) further comprises dispersing a sealing medium at the periphery of the occluded lesion which contacts the edge of the spacer but is not covered thereby.

According to one embodiment, connecting the plurality of inlet tubes to at least one reservoir by a fluid communication, provides a liquid-impermeable seal around the occluded lesion. According to yet another embodiment, the method further comprises connecting the at least one outlet tube to a collecting reservoir, said collecting reservoir being configured to hold fluids draining from said at least one outlet tube. According to another embodiment, connecting the at least one outlet tube to a collecting reservoir provides a gas-impermeable seal around the occluded lesion. According to yet another embodiment, the gas-impermeable seal is vacuum-proof.

According to another embodiment, the method further comprises providing a control means being in fluid communication with at least one inlet tube of said plurality of inlet tubes and with the at least one reservoir, thereby initiating a controlled flow of fluids from the at least one reservoir through the at least one inlet tube. According to yet another embodiment, the control means is selected from the group consisting of: a peristaltic pump and a drip counter.

According to an alternative embodiment, the method further comprises positioning the at least one reservoir on a higher level than the lesion, thereby initiating flow of debriding solution from the at least one reservoir through the plurality of inlet tubes to the lesion by gravitation. According to another alternative embodiment, the method further comprises providing a plurality of control means, each control means being in fluid communication with a corresponding inlet tube of the plurality of inlet tubes and with the at least one reservoir, thereby controlling the flow rate within each inlet tube independently by a separate control means. According to yet another embodiment, the control means is a clip or a drip chamber.

According to an alternative embodiment, the method further comprising positioning the at least one reservoir and the collecting reservoir at predetermined levels with respect to the occluded lesion and with respect to one another, thereby generating pressure at the occluded lesion. According to yet another embodiment, the method further comprises generating a negative pressure at the occluded lesion.

According to yet another embodiment, the flow of the solution from the at least one reservoir through the plurality of inlet tubes has a rate within the range of 1 ml/hour to 10 ml/hour. According to yet another embodiment, the flow of the solution from the at least one reservoir through the plurality of inlet tubes continues for 30 minutes to 6 hours.

According to another embodiment, the method further comprises providing at least one element being in fluid communication with the at least one reservoir and at least one inlet tube of the plurality of inlet tubes, the element is selected from the group consisting of: a control means adapted for controlling the rate of flow from the at least one reservoir to the at least one inlet tube; a separator being in fluid communication with at least one inlet tube of said plurality of inlet tubes and with the at least one reservoir, thereby to reversibly disconnect and reconnect said at least one inlet tube from said at least one reservoir; a connector adapted for opening and closing the fluid communication between the at least one reservoir and the at least one inlet tube; a filter for filtering a solution flowing within the at least one inlet tube, a mixing means for mixing the solution within the at least one reservoir; a thermo-regulating means for affecting the temperature of the solution within the at least one reservoir; a vacuum source being in fluid communication with the at least one outlet tube, adapted for generating a negative pressure at the occluded skin lesion; and a collecting reservoir being in fluid communication with the at least one outlet tube configured to collect the fluids drained from the proximal end of said at least one outlet tube.

Other objects, features and advantages of the present invention will become clear from the following description and drawings.

BRIEF DESCRIPTION OF THE DRAWINGS

FIG. 16 exhibits burns in skin sections before (A) and after application of a streaming solution comprising collagenase and thermolysin (B); and FIG. 17 shows burns in skin sections before (A) and after application of a streaming solution comprising papain (B).

DETAILED DESCRIPTION OF THE INVENTION

Definitions

Figure 1A:
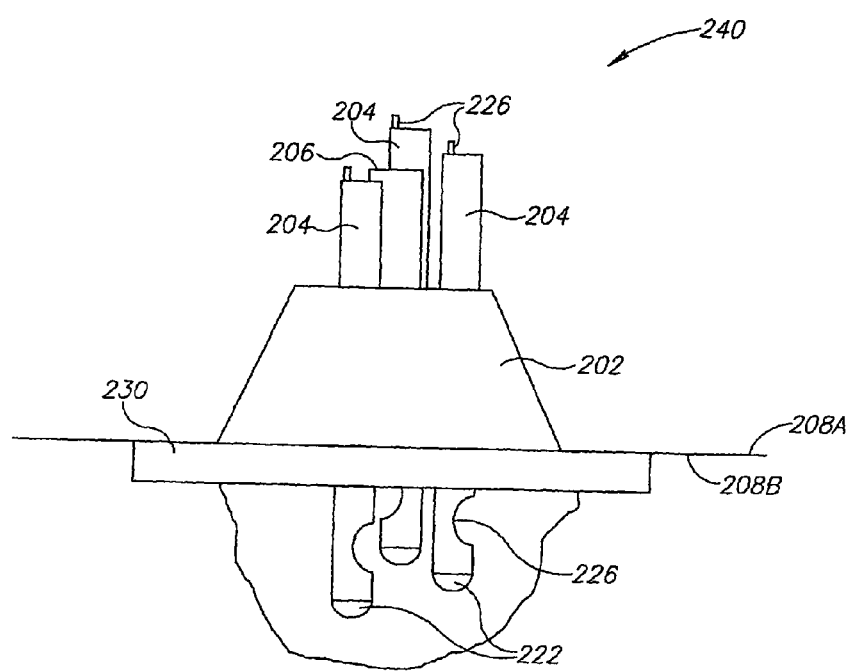
FIGS. 1A and 1B are schematic isometric and side views of the apparatus, constructed and operative in accordance with an embodiment of the invention.

The terms "skin lesion" and "lesion" are interchangeable used herein to describe damaged skin comprising devitalized tissue, including but not limited to, chronic cutaneous ulcers (e.g. diabetic ulcers and decubitus ulcers) and burns. The skin lesion may extend through all or through part of the skin layers and may further extend through the underlying muscles and tissues.

"Stage X" is commonly used to classify skin lesions. Lesion types are classified in stages according to the severity of the lesion. The staging system applies to burn wounds, decubitus ulcers and several other types of ulcers and lesions. STAGE I is a superficial lesion characterized by a surface reddening of the skin. The skin is unbroken. This lesion may be, inter alia, a beginning decubitus ulcer and tends to heal spontaneously when pressure is relieved on the area. STAGE II is characterized by a blister either broken or unbroken wherein at least a partial layer of the skin is injured. Stage II decubitus ulcer or pressure wound may develop into Stage III decubitus ulcer or pressure wound. STAGE III lesion extends through all of the layers of the skin and may involve a serious infection. STAGE IV lesion extends through the skin and involves underlying muscle, tendons and bone. This type of lesion can produce a life threatening infection if not aggressively treated. STAGE V is an older classification of a lesion that is extremely deep, having gone through the muscle layers and involving underlying organs and bone. Amputation may be necessary is some situations.

The term "devitalized tissue" as used herein refers to necrotic tissue or eschar, from cutaneous ulcers or burns which consists of a complex mixture of dried blood, purulent exudates, and denatured proteins normally found in the epidermal and dermal skin layers. The denatured proteins are primarily collagen, elastin, fibrin, hemoglobin, and other coagulated proteins. Collagen comprises about 75% of the skin's dry weight and is the main constituent of the necrotic debris and of eschar. Strands of semi-viable, compromised collagen, whose protective mucopolysaccharide sheath has been damaged or destroyed, anchor the necrotic tissue to the wound surface. These strands must be fully eliminated in order for the necrotic material to be separated from its base. This complete debridement then permits development of granulation tissue during the healing process.

The term "debridement" as used herein refers to the process of removing the non-viable tissue from a lesion to prevent infection and to facilitate healing as healing of lesion is a complex process which is often further complicated by the presence of non-viable, necrotic tissue in the wound bed.

The term "wound bed preparation" as used herein is to be construed in its most general sense and refers to the global management of the wound to accelerate endogenous healing or to facilitate the effectiveness of therapeutic modalities. Wound bed preparation of acute wounds includes debridement and removal of necrotic tissue and bacteria. In chronic wounds, wound bed preparation is more complicated as most of the necrotic matter cannot not be easily accessed, and since the preparation further includes removal of exudates.

Preferred Modes for Carrying out the Invention

The present invention relates to an apparatus and methods for treating skin. The apparatus provides a continuous flow of therapeutic solutions into the wound bed of the skin lesion, through a plurality of adjustable inlet tubes. The plurality of inlet tubes is adjustable in position and in angle with respect to the skin lesion, thereby continuously supplying therapeutic solutions to any desired depth and at any angle.

The present invention is generally applicable for the controlled removal and retrieval of cells from skin lesions, including, but not limited to, pressure ulcers and chronic open wounds such as decubitus ulcers and diabetic ulcers. Preparing the wound bed of chronic wounds requires both, an efficient enzymatic debriding of necrotic matter and a continuous removal of exudates (Falanga, Wounds, 14:45-57, 2002). The necrotic matter in chronic wounds cannot be easily accessed. Moreover, chronic wounds may produce substantial amounts of exudate, which was shown to inhibit the proliferation and function of key resident cells and to contain proteases that break down extracellular matrix proteins. Thus, the present invention is specifically applicable for treating chronic skin lesions as it provides particularly efficient enzymatic debridement of devitalized tissue within and on the surface of the lesions together with continuous removal of exudates, debris and therapeutic solutions from the site of the lesions. The device of the invention is adapted for streaming a solution of debriding enzymes at any angle and depth, in order to convey the enzymatic solution into areas that are not readily accessible.

It is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1B:
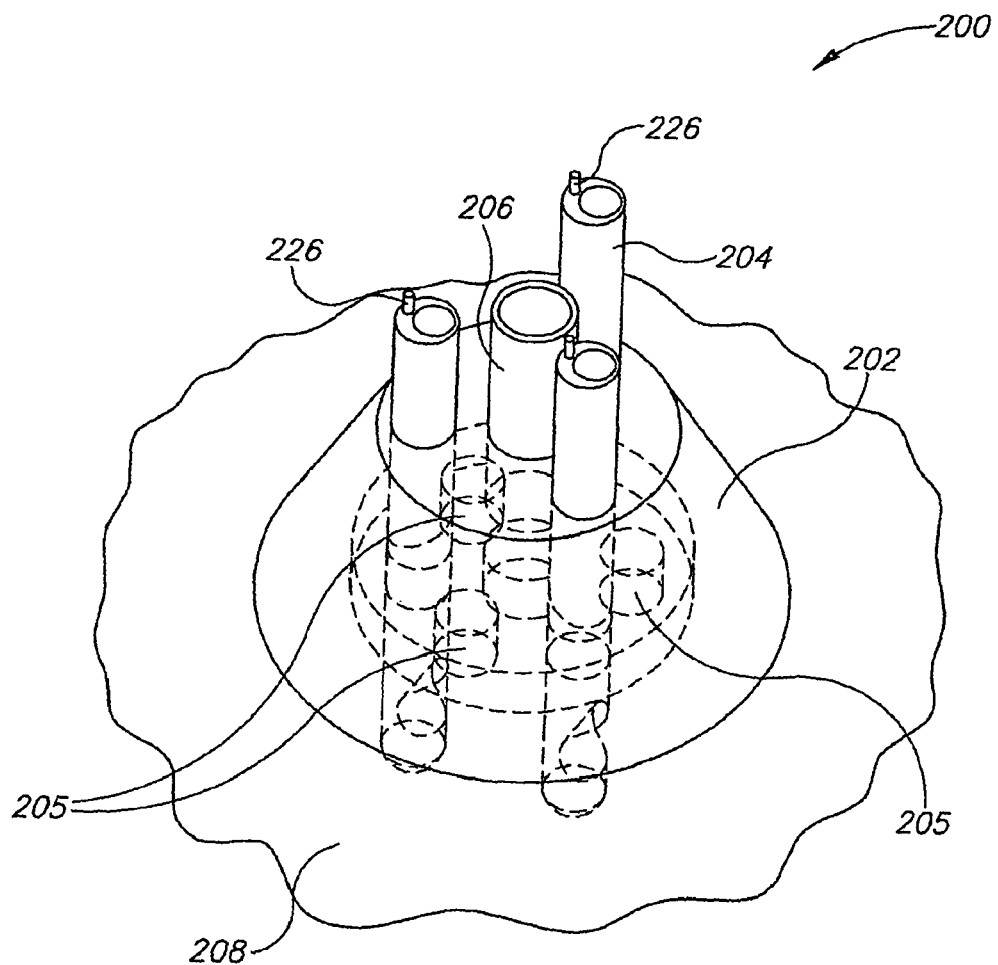
Figure 2:
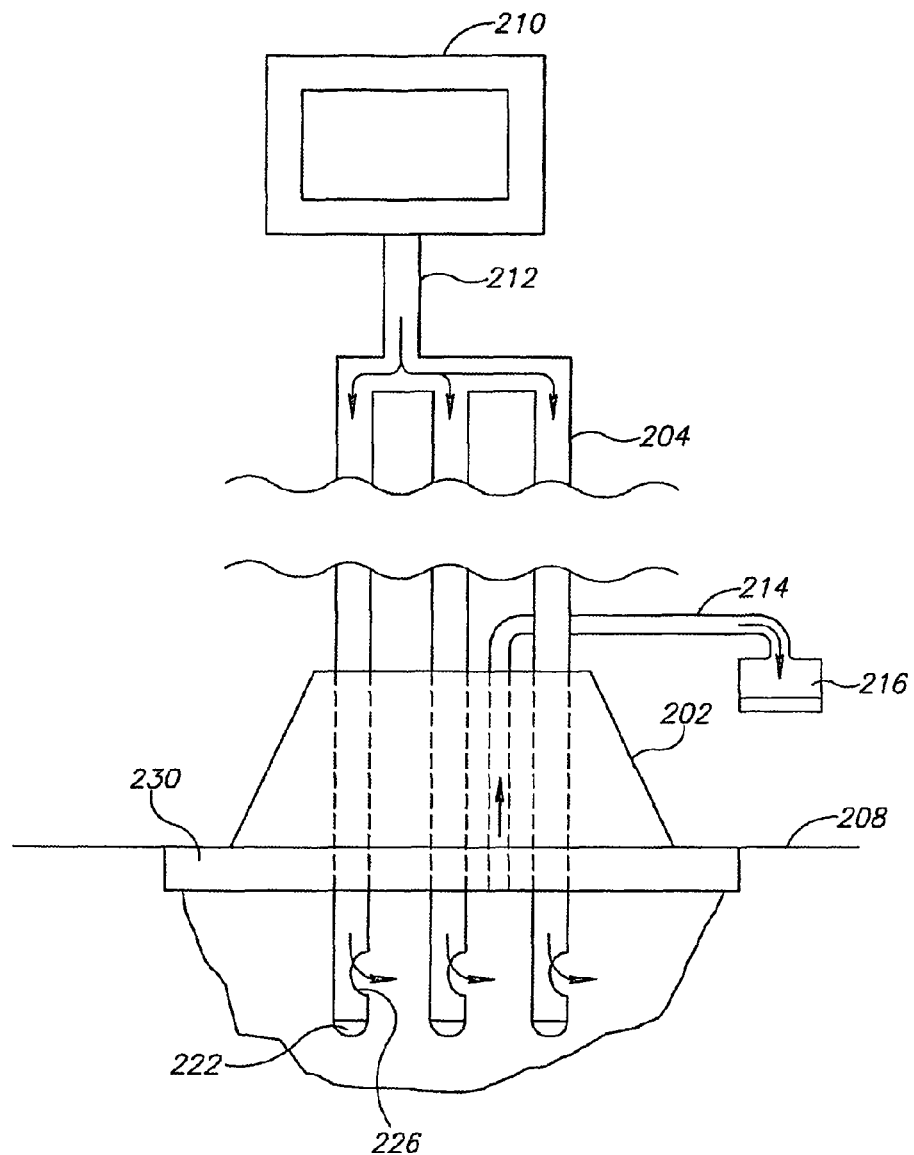
FIG. 2 is a schematic illustration of a system for dispensing (or streaming) and collecting the therapeutic solution utilizing the apparatus of FIGS. 1A and 1B.

Reference is now made to FIGS. 1A, 1B and 2, which are schematic illustrations of an applicator, generally designated 200, constructed and operative in accordance with an embodiment of the invention to provide a continuous flow of therapeutic solutions into the wound bed of a skin lesion.

FIGS. 1A and 1B are schematic isometric and side views of the applicator 200. FIG. 2 is a schematic illustration of a system for dispensing (or streaming) and collecting the therapeutic solution utilizing the applicator 200 of FIG. 1.

The applicator 200 comprises a housing unit 202 configured to hold a plurality of inlet tubes 204 and at least one outlet tube 206. The housing unit 202 may further comprise multiple drainage openings 205 being in fluid communication with the at least one outlet tube 206. Thus, fluids accumulating at the occluded lesion and within the housing unit, may be collected by drainage openings 205 and to the outlet tube 206. The applicator 200 further comprises means for affixing 208 the applicator 200 to the skin around the circumference of a skin lesion, such as an ulcer. The means 208 may be connected to housing 202 or may be attached extemporaneously to the housing upon affixing the applicator to the skin surrounding a skin lesion.

The applicator 200 may be connected to a reservoir 210 in which the therapeutic solution may be stored. The therapeutic solution may be administered via an inlet port 212 and may be collected via at least one outlet port 214 into a cell and waste collector 216, for example, as will be described in further detail hereinbelow. Moreover, the plurality of inlet tubes and the at least one outlet tube can be configured in a wide variety of arrangement to accommodate various lesion at various sites. For example, multiple inlet tubes 204 may be connected to a single reservoir 210 and vice versa.

The housing 202 may comprise suitable shape and configuration for securing a plurality of tubes including inlet tubes 204 and outlet tube 206. In the exemplary embodiment illustrated in FIGS. 1A and 1B, housing 212 comprises a conical shape, having a wider diameter proximal the wound bed. Housing 212 comprises a plurality of apertures 220, each aperture configured to match the diameter of its corresponding inlet and/or outlet tube. It will be appreciated by persons knowledgeable in the art that a single aperture may be used to restrain the plurality of inlet and/or outlet tubes.

Each of the plurality of inlet tubes 204 may be configured to be adjustable in position and angle with respect to the housing unit 202, thereby allowing the therapeutic solution to be administered to a specific part of the wound bed. Thus the inlet tubes are capable of penetrating deeply into the lesion and are suitable for infusing areas that are not normally readily accessible.

The distal end 222 of the inlet tube 204 may be configured to face the skin lesion and the distal end 222 may be smoothly curved to form a non-traumatic tip. Furthermore, the opening 224 at the distal end 222 of the inlet tube 204 may be formed within any part of the inlet tube 204, such as in its end or along the length of the tube, as illustrated in example of FIG. 1A.

The inlet tubes 204 may be constructed from any suitable material such as a flexible elastomer including silicone, polyurethane, natural rubber, neoprene and ethyl vinyl acetate, for example. Each inlet tube may be colorless and transparent which enables the operator to view the quality and consistency of the fluid being transferred to the wound bed.

In an embodiment of the invention, the inlet tubes 204 may be configured to be extendable or retractable along their longitudinal axes, as is known in the art. For example, an adjustable screw mechanism may be adapted to each of the inlet tubes thereby to extend or retract each inlet tube along its longitudinal axis.

Similarly, the outlet tube may be configured to be extendable or retractable along their longitudinal axes, as is known in the art.

Preferably, each inlet and outlet tube should be fitted with a suitable sealing unit, such as an "O" ring, for example, to prevent the passage of fluids between the external diameter of the tubes and its corresponding aperture.

The affixing means 208 may comprise any suitable adhesive means, known in the art, for adhering the applicator 200 to the skin being treated. Affixing means 208 may comprise a first plane 208a, which is suitably attached to the housing 202 and a second plane 208b configured to adhere to the skin. Preferably, the dimensions of the affixing means 208 are larger than the wound bed being treated to ensure that the solution being administered to the wound bed remains within the wound bed. Means 208 may be made of a flexible material, for example, an adhesive film, capable of conforming to the anatomy at the location of the lesion. In some embodiments, the first plane 208a also comprises adhesives.

The adhesive means may be biocompatible and the lower plane of the affixing means 208 may be covered with a protective detachable film, which is removed prior to attachment of the applicator 200 to the skin at the circumference of the wound bed.

In an embodiment of the invention, each of the inlet tubes 204 may comprise a suitable deflectable wire 226, which extends along the longitudinal axis of the inlet tube 204 and is suitably connected thereto. The deflectable wire enables to maintain the angle and shape of the inlet tube 204 throughout the treatment. The deflectable wire 226 may be configured so as not to extend beyond the distal end (adjacent the wound bed) of the inlet tube 204. The deflectable wire may be formed from a rigid material that is flexible and elastic, such as silver, platinum, stainless steel and polymer, for example.

The inlet tubes 204 may comprise a longitudinal first lumen separated from the major lumen of said tubes, which is configured to hold therein deflectable wire 226.

The applicator may comprises a control means being in fluid communication with at least one inlet tube and with the at least one reservoir, the control means is adapted to control the flow rate of fluids flowing from the at least one reservoir through the at least one inlet tube. The control means may be selected from the group consisting of: peristaltic pump and a drip counter. The flow rate determined by the control means is any rate which is required to replace the enzymatic solution at the occluded lesion site with a fresh solution of catalytically active enzymes. The flow rate may be within the range of 1 ml/hour to 10 ml/hour. Slower or faster flow ranges are also included within the scope of the present invention, providing that the rate is adapted to provide an effective debridement of the devitalized tissue of the skin lesion.

According to yet another embodiment, the applicator further comprises a vacuum source being in fluid communication with the at least one outlet tube, thereby generating a negative pressure at the occluded skin lesion. Vacuum application at the wound site was shown to have therapeutic value in the process of wounds healing as disclosed for example in U.S. Pat. Nos. 6,135,116; 6,695,823; 6,767,334 and US Patent Applications, Publication Nos. 20020143286; 20030040687 and 20030050594 among others, all of which are assigned to KCl Licensing, Inc. However, vacuum alone in the absence of efficient debridement, cannot contribute to wound bed preparation of chronic wounds or to wound bed preparation of acute wounds containing necrotic matter within the wound and not only on its surface. Necrotic tissue is not a constant phenomenon that disappears once removed, rather necrotic tissue keeps accumulating in skin lesions due to ongoing programmed cell death (apoptosis) that occurs in the lesions (Falanga, ibid). In pressure ulcers for example, there are constant cycles of adequate blood flow or decreased edema cycle with periods of ischemia (from pressure) and increasing edema. Thus, the necrotic material that is periodically accumulated within wounds needs to be removed.

According to yet another embodiment, the applicator further comprises a thermo-regulating means being in communication with the at least one reservoir, thereby to affect the temperature of fluids held in said at least one reservoir. According to another embodiment, the applicator further comprises a thermo-regulating means being in communication with at least one inlet tube of said plurality of inlet tubes, thereby to affect the temperature of fluids flowing through said at least one inlet tube.

According to yet another embodiment, the applicator further comprises at least one filter fitted within at least one inlet tube of said plurality of inlet tubes, for filtering fluids flowing within said at least one inlet tube.

In a further embodiment of the invention, there is provided apparatus 240 for treating skin lesion, the apparatus comprises the applicator 200 and further comprises a spacer 230 secured to the skin surface about the lesion circumference for occluding an area comprising the lesion. The spacer 230 may comprise a resilient liquid-impermeable material, known in the art, or an elastomer, such as a foam-like material, for example. The spacer 230 may comprise any suitable material such as silicone, silicone foam, polyurethane, natural rubber, neoprene and ethyl vinyl acetate foam, for example.

One face of the spacer 230 may be suitably affixed to the housing, while the lower face comprises suitable means for affixing the spacer 230 to the skin, formed from a suitable material such as thermoplastic resin, pressure sensitive adhesive, hydrocolloid adhesive and rubber, for example. The means for affixing the spacer 230 to the skin and to the applicator may be covered with protective detachable films to be removed upon attachment of the spacer to the skin and to the applicator.

Reference is now made to FIGS. 3-12, which are schematic illustrations of an apparatus 80 and an applicator 24 for streaming and collecting a solution containing an effective amount of protease over, and through a skin lesion.

Figure 3:
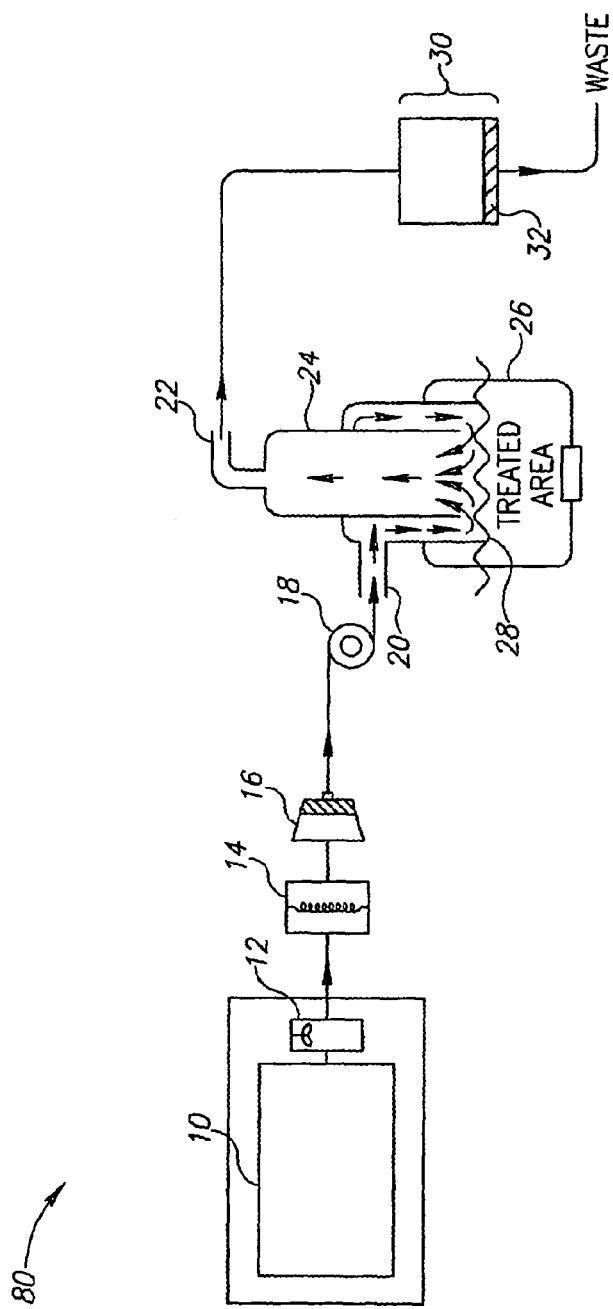
FIG. 3 is a cross-sectional view of a device in accordance with one embodiment of the present invention.

One embodiment of apparatus 80 is illustrated in FIG. 3. Apparatus 80 according to this embodiment, comprises a first reservoir 10 for holding a solution containing an effective amount of at least one protease. First reservoir 10 may be constructed of durable, inert, non-porous material for repetitive uses, such as glass, metal or plastic. First reservoir 10 may be sanitized between uses by methods well known to one skilled in the art, including by moist or dry heat, or the use of antiseptics, gas or radiation. In another preferred embodiment, first reservoir 10 is constructed of non-durable, disposable material such as metal foil, plastic or foil-laminated or impregnated cardboard or paper, for single use, sterilized and sealed for storage. Dimensions of first reservoir 10 may be adequate for containing a volume of protease solution sufficient to complete a single enzymatic surgery procedure, or smaller, necessitating replenishment during the procedure. First reservoir 10 is typically about one liter in volume, but may vary from 100 milliliters to several liters.

In a preferred embodiment, a mixer 12 for mixing the protease solution is in fluid communication with first reservoir 10, for preventing inconsistent distribution of the protease solution ingredients. Mixer 12 may be external to first reservoir 10, or indwelling. Mixing may be accomplished by rotary motion, as of an impeller or vane within a chamber, or by a rocking or turning oscillatory motion, as of a rocking or rotating platform.

In another preferred embodiment, first reservoir 10 is in fluid communication with a thermoregulator 14, for heating and/or cooling the protease solution to optimal temperature for activation of catalytic activity. Thermoregulator 14 may be a radiantly or convection-heated open chamber, receiving the stream of protease solution, or, preferably a heated and/or cooled fluid bath or solid block receiving a fluid communication element, such as glass or plastic tubing, eliminating direct fluid contact of the stream of protease with thermoregulator 14 and reducing risk of contamination of the protease solution with desired contaminants.

As used herein the phrase "in fluid communication" refers mainly to the capability of selective or non-selective transfer of fluid and/or semi-fluid substances between the specified elements. Such transfer may be accomplished by, for example, channels, tubes, membranes, conduits, pores and/or capillaries.

In yet a further embodiment of the present invention, first reservoir 10 is in fluid communication with a filter 16 which serves for sterilization of the protease solution prior to its application. Filter 16 is preferably a sealed (except for inlet and outlet ports), sterilized housing containing a filtering member excluding particles greater than, for example, 0.25 microns, eliminating common bacterial contamination. One such commercially available filter is distributed under the name Complete Sterifil System (Sigma Chemical Company, Inc.). In a further embodiment of the present invention, first reservoir 10 is in fluid communication with a pump 18 which serves for streaming the protease solution from first reservoir 10 to an applicator 24 (illustratively described in detail hereinbelow) under positive pressure. Thus, the protease solution is delivered to the site of treatment with sufficient force to effect a mechanical, "stripping" action in addition to the enzymatic digestion of matrix proteins. The novel combination of a directional, mechanical force and enzymatic disruption of the lesion tissue provided by the present invention enables the removal of cells and tissue from the treated surfaces.

Pump 18 may be an air pump, a piston-driven fluid pump, syringe pump or an impeller. In one embodiment of the present invention, pump 18 is preferably a variable-speed peristaltic pump, operating through pressure on a flexible fluid communication element eliminating direct fluid contact with the protease solution and subsequent risk of contamination. The variable speed feature further affords control of the intensity of the stream of protease solution applied to the dermatological lesion. One such commercially available peristaltic pump is distributed under the name Masterflex Economy (Aldrich Chemical Company, Inc.). In an alternative embodiment of the present invention, streaming the protease solution is effected by gravitation assisted by elevating first reservoir 10 substantially above other elements in fluid communication therewith.

In general, applicator 24 is for streaming a solution over, and in contact with, a skin portion. Applicator 24 includes a housing having a skin-facing opening, at least one inlet and at least one outlet. The at least one inlet and the at least one outlet each providing a passageway for streaming of the solution therethrough and over the skin portion defined by the skin-facing opening, wherein an opening of at least one of the at least one inlet and the at least one outlet through which the solution streams is height adjustable, such that applicator 24 physically conforms to a non-smooth skin surface.

The term "height" as used herein refers to the length of the inlet tube that extends beyond the opening 108 towards the lesion. This length may also correspond to the distance between opening 108 and the tip of the inlet tube which faces the lesion.

Applicator 24 is in fluid communication with first reservoir 10, and is designed and constructed to restrict the stream of the protease solution over, and in contact with the skin portion undergoing treatment. Applicator 24 comprises two ports, inlet port 20 serves for receiving the protease solution from first reservoir 10, and outlet port 22 which serves for removing the protease solution and cells from the treated dermatological lesion. Applicator 24 further comprises a recessed skin-facing surface 28, enclosed by the downward projecting outer rim of applicator 24, creating a confined, local area of treatment, preventing exposure of neighboring tissue to proteolytic activity.

Figure 10:
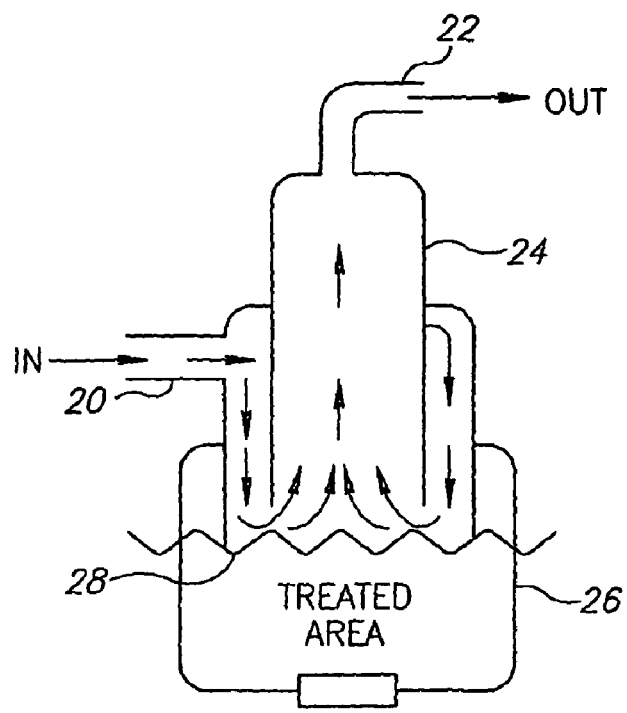
FIG. 10 is an enlarged, cross-sectional view of the protease solution applicator and engaging mechanism according to the present invention.
Figure 11:
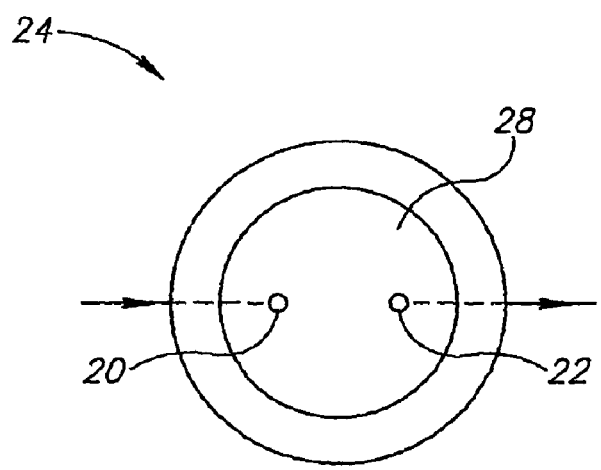
FIG. 11 is an enlarged, bottom (skin-facing surface) view of the protease solution applicator, including the protease solution inlet and outlet ports, according to the present invention.
Figure 12:
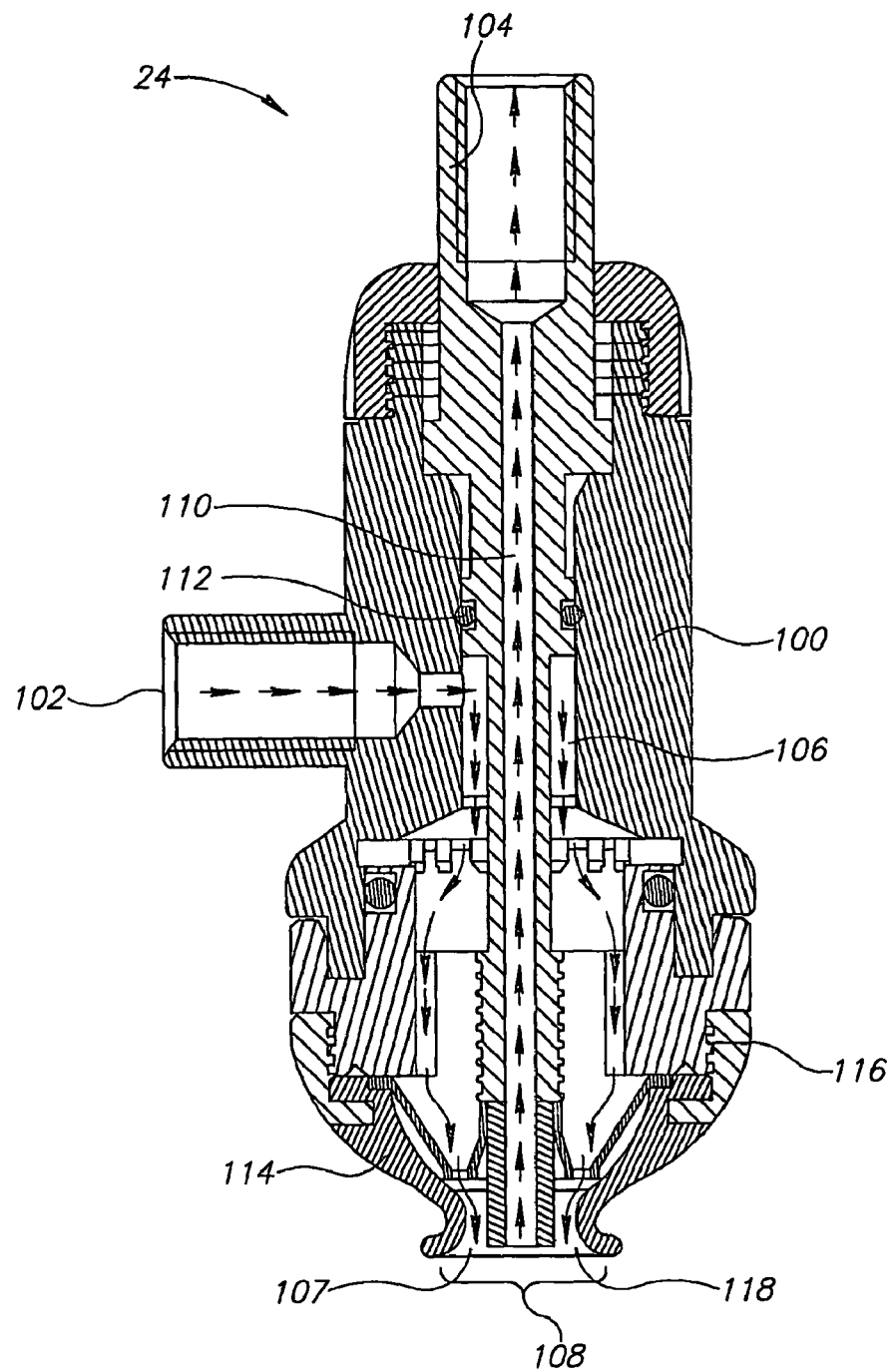
FIG. 12 is a cross sectional view of an exemplary specific preferred embodiment of the applicator included in the device of the present invention, which is applicable for practicing the present invention on skin.

One embodiment of applicator 24 is illustrated in FIGS. 10-12. Inlet port 20 and outlet port 22 provide directional fluid motion for the stream of protease solution, enabling a mechanical "stripping" effect enhancing the enzymatic disruption of the intracellular matrix and removal of cells from the treated lesion surface. Applicator 24 may be engaged with the skin surface by skin-ward pressure applied by attendant operators or treated subject, weight, adhesive connection to adjacent skin surfaces or other means, suitable for the body part bearing the lesion to be treated. In one preferred embodiment applicator 24 comprises an engaging mechanism 26, which comprises two or more flexible elements adjustably connected to allow encirclement of a cylindrical body part (such as a limb or torso) and application of skin-ward pressure through tension, such as a strap and buckle or toothed belt fastener.

Applicator 24 may be constructed of durable, non-porous material including, but not limited to, glass, metal, plastic or rubber, and may be reusable or preferably disposable. Applicator 24 is preferably capable of sterilization by gas, chemicals, moist or dry heat, or radiation, and is supplied sealed and sterilized for use. In one alternative embodiment, applicator 24 is a "push-pull" cannula typically employed in tissue perfusion techniques, for example, as described by Arancibia, S., in "Push-pull Perfusion Technique In Neuroendocrinology", Ann. Endocrinol. (Paris) 48, 410-18 (1987), which comprises an inflow tube recessed within a wider, outflow tube, creating localized flow of protease solution confined to the outer diameter of the wider, outflow tube.

Reference is now made to FIG. 10, a cross sectional view of an exemplary embodiment of an applicator included in the apparatus of the present invention. Applicator 24 includes a housing 100 having an inlet 102 and an outlet 104. Fluid entering through inlet 102 is directed via a first tube structure 106 to a treatment zone 107 defined by a somewhat conical silicone structure 114 having a skin-facing opening 108, 9 mm in diameter. A second tube stature 110 positioned within first tube structure 106 is used to direct fluid from treatment zone 107 to outlet 104. An O-ring 112 is used to restrict flow to the intended direction within first tube structure 106 A screw mechanism 116 allows adjustment of the height of opening 118 of second tube structure 110 with respect to skin-facing opening 108 of treatment zone 107. Preferably, a pump, as illustratively described hereinabove, is used to direct fluid from a reservoir into inlet 102. A drainage tube is used to drain fluid from outlet 104.

According to the present invention apparatus 80 preferably further comprises a cell collector 30 which is in fluid communication with first reservoir 10 and applicator 24, and which serves for receiving the protease solution and cells removed from the treated lesion surface, and for providing outflow of waste fluid or fluid to be recycled through apparatus 80. Collected cells are thus made available for histological examination and/or cell culture procedures. In one preferred embodiment cell collector 30 comprises a filter 32 for collection and separation of cells removed from the dermatological lesion. Collector 30 and filter 32 are preferably supplied as a sterile, disposable modular element, such as the Complete Sterifil System (Sigma, Israel). In a further embodiment of the present invention, which is specifically illustrated in FIG. 4, separation of the fluid and cellular fractions in cell collector 30 is effected by continuous flow centrifuge 40. Continuous flow centrifugation provides increased liquid handling capacity, removing the protease solution outflow quickly upon arrival from applicator 24 and concentrating lesion cells for examination and/or culturing.

It will be appreciated, in the context of the present invention that lesion cells collected by cell collector 30 are exposed to protease activity during separation from the fluid component of the protease stream arriving at cell collector 30. Preservation of the cells' morphological and metabolic integrity, and therefore diagnostic value, may depend, in part, on limitation of their prolonged contact with protease. Thus, in one preferred embodiment of the present invention, cell collector 30 is constructed to allow removal and/or sampling of collected cells in mid-process. This may be effected by periodic cessation of streaming of protease solution through applicator 24, removal of the filter element of filter 32, and replacement with a fresh filter element. Alternatively, the entire cell collector 30 may be replaced during operation with a fresh cell collector unit. Where continuous flow centrifuge 40 is the means of cell collection, centrifuge operation may be periodically halted to allow removal of the collected cells from the centrifuge rotor. More preferably, the centrifuge will provide a continuous outflow of concentrated cells for examination and/or cell culture.

It will be noted that the fluid outflow from cell collector 30 contains largely still active protease solution, devoid of the cellular and tissue debris fractions removed by filter 32 and/or centrifuge 40 which may be recycled for reuse. Thus, in one preferred embodiment the fluid outflow of cell collector 30 is reintroduced to the stream of at least one protease solution "upstream" of applicator 24 and pump 18. Fluid communication between the cell collector outflow and the stream of protease solution may be effected by a one-way valve connection, ensuring uni-directional streaming of fluid towards applicator 24. Thus, significant economy of operation is achieved by reuse of the cell collector 30 outflow, effectively reducing the volume of protease solution required per treatment.

Additional embodiments of enzymatic surgery apparatus 80 are depicted in FIGS. 5-9; in each case thermoregulator 14, filter 16, pump 18, applicator 24 and cell collector 30 are substantially as described in the preceding sections.

Figure 5:
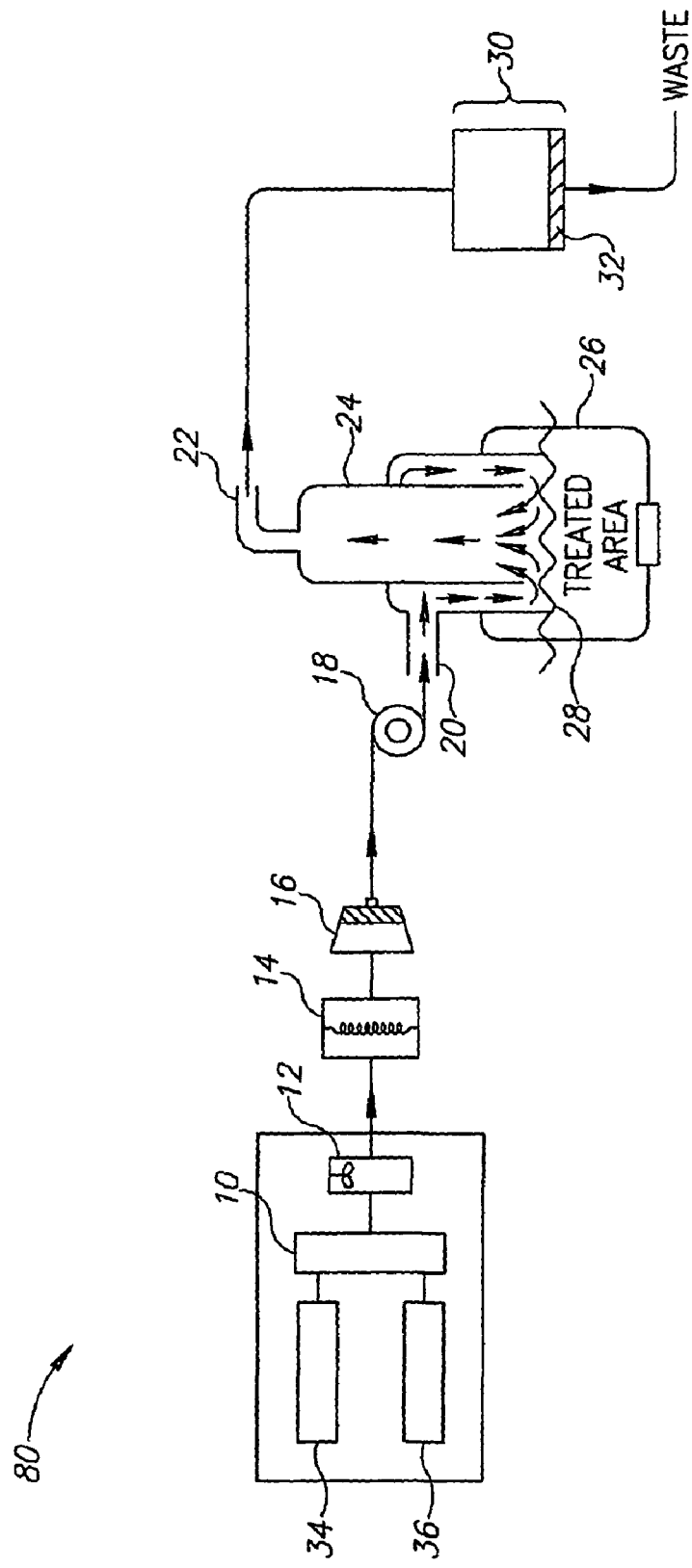
FIG. 5 is a cross sectional view of a device in accordance with yet another embodiment of the present invention.

In one embodiment, illustrated in FIG. 5, apparatus 80 comprises, in addition to first reservoir 10, a second reservoir 34 and a third reservoir 36, which serve for containing a first, substantially inactive protease solution and a second, protease activating solution, respectively. Thus, the protease solution may be prepared and stored in a stabilized, inactive form prior to use, acquiring substantial catalytic activity only after admixing with the activating solution in first reservoir 10.

Figure 6:
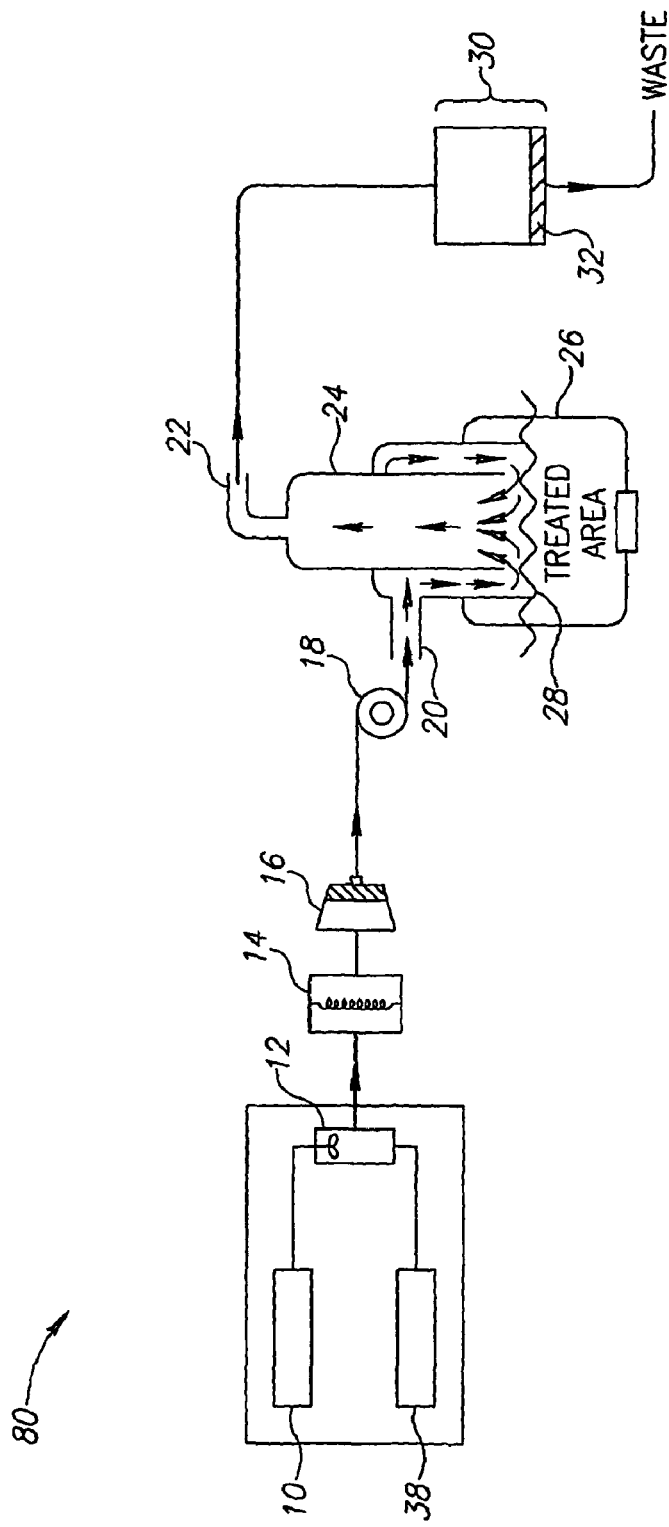
FIG. 6 is a cross sectional view of a device in accordance with sill another embodiment of the present invention.

In yet a further embodiment, illustrated in FIG. 6, enzymatic surgery apparatus 80 comprises first reservoir 10 and second reservoir 38, for containing a first, substantially inactive protease and a second, activating solution, respectively. Thus, powdered, lyophylized, and/or other, non-aqueous, stabilized protease preparation(s) placed in first reservoir 10 may be stored until use, minimizing autolysis and loss of catalytic activity. First 10 and second 38 reservoirs are in fluid communication, providing a catalytically active protease solution upon mixing of their contents by mixer 12.

Figure 7:
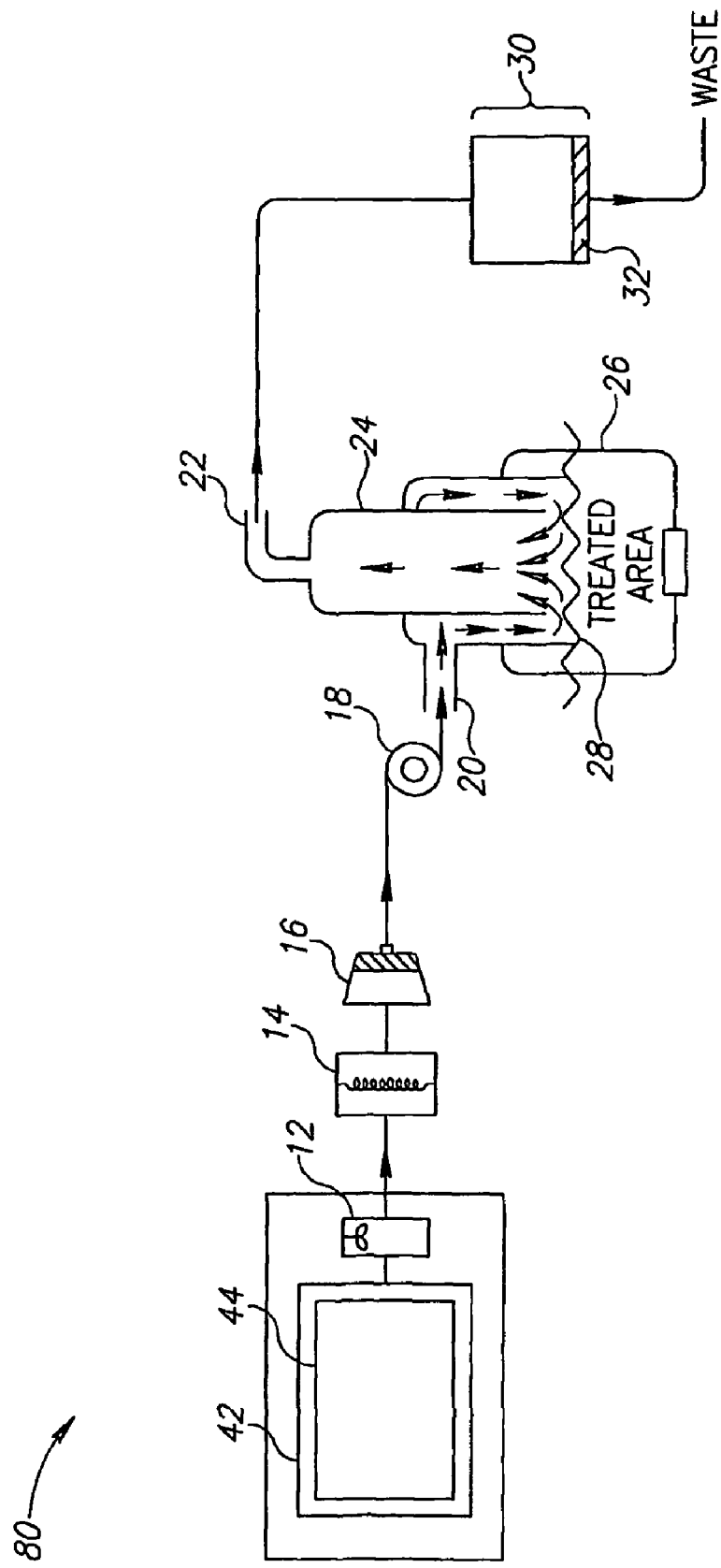
FIG. 7 is a cross sectional view of a device in accordance with an additional embodiment of the present invention.
Figure 8:
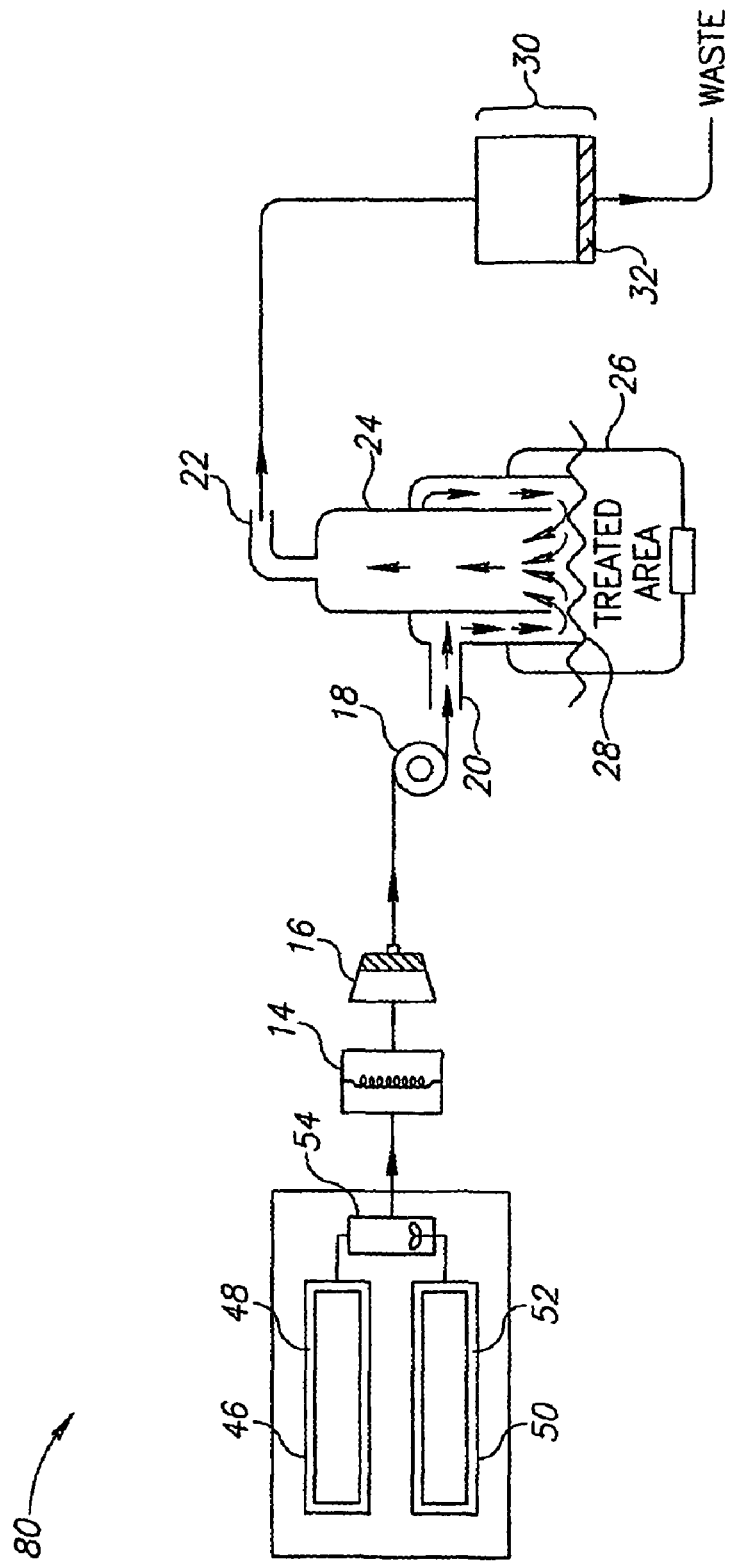
FIG. 8 is a cross sectional view of a device in accordance with yet an additional embodiment of the present invention.
Figure 9:
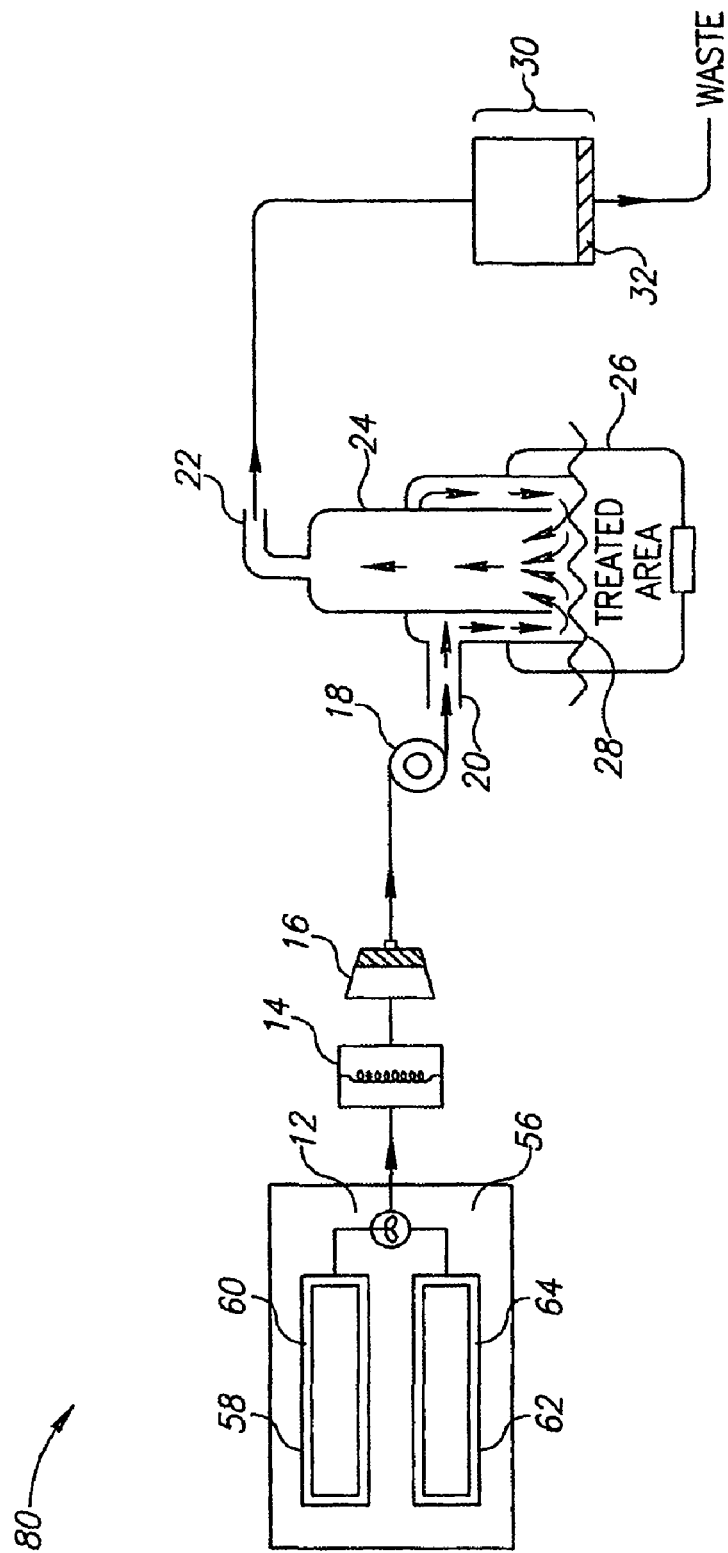
FIG. 9 is a cross sectional view of a device in accordance with still an additional embodiment of the present invention.

FIGS. 7-9 depict enzymatic surgery apparatus 80 designed to receive prepared reservoirs or ampoules of protease, protease solution and/or protease activating solution. In one embodiment, illustrated in FIG. 7, a receptacle 42 is designed to receive modular reservoir or ampoule 44, containing catalytically active protease solution, effecting fluid communication with applicator 24, cell collector 30 and additional "downstream" elements of apparatus 80. Thus, apparatus 80 may be operated with standardized, pre-prepared, stored protease solution(s), increasing simplicity of use and accuracy of protease activity delivered, and decreasing risk of contamination of treated skin surfaces.

As used herein in the specification and in the claims section below, the terms "reservoir" and "ampoule" interchangeably refer to a separate, enclosed container capable of establishing fluid communication with other containers, receptacles or devices. Such reservoirs or ampoules typically contain fluids or fluid-like substances, and may be designed to be accurately engaged by a complementary receptacle or housing. Sealed reservoirs or ampoules provide convenient, standardized means of preparation and storage of active solutions and reagents for the operation of, for example, enzymatic surgery apparatus 80.

In yet another embodiment, illustrated in FIG. 8, first receptacle 46 receives first modular reservoir or ampoule 48, which contains inactivated, stabilized protease solution, while second receptacle 50 receives second modular reservoir or ampoule 52, which contains a protease activating solution. First receptacle 46 and second receptacle 50 are in fluid communication with a mixing chamber 54, which serves for providing fluid contact and mixing of the contents of first reservoir 48 and second reservoir 52, activating the stabilized, inactivated protease. A mixer 12 as described above can be placed within mixing chamber 54.

In another embodiment, illustrated in FIG. 9, first receptacle 58 receives first modular reservoir or ampoule 60, which contains stabilized, inactive, protease preparation in powder, lyophilized and/or other non-aqueous form. Second receptacle 62 receives second modular reservoir or ampoule 64, which contains the activating solution. First receptacle 58 and second receptacle 62 are in fluid communication with mixing mechanism 56, providing contact between and effect dispersal of the non-aqueous protease preparation in the activating solution.

Conventional mechanical and non-mechanical methods of treating and removal of skin lesions such as razor-blade or scalpel excision, $CO_2$ laser surgery, cryosurgery, electrocauterization, and electroablation are associated with pain, stress trauma, bleeding, scarring, contamination, hyperpigmentation and disruption of adjacent and underlying tissue. The milder proteolytic digestion of skin lesions and wounds has been shown to provide superior healing of such lesions, with decreased incidence of scarring, bleeding and contamination. Indeed, protease preparations are commonly used to promote healing and reduce the scarring of $CO_2$ laser surgery wounds.

The ability of proteases to gently disrupt the integrity of dermal tissue has led to the therapeutic use of proteolytic enzymes as an adjunct, or alternative to mechanical or laser surgical treatment of skin lesions. In order for such enzymatic treatment to overcome the abovementioned disadvantages of surgical, electrosurgical, cryosurgical and laser-surgical methods (pain, scarring, traumatic stress, hyperpigmentation and destruction of neighboring tissue), it is desirable for the proteolytic method to readily and thoroughly hydrolyze a wide variety of proteins found in skin lesions; function at physiological pH and temperature; be compatible with adjunct therapies (e.g., anesthetics, cleansing agents, topical antibiotics); and not interfere with normal wound heating or complicate skin grafting. In addition, it is important to provide means of retention and preservation of the viability of the isolated, removed cells for histological examination or cell culture; to allow for localized and confined application of the protease and provide for stability of the enzyme formulations from the effects of pH, temperature and autoproteolysis.

These and other beneficial considerations are addressed, for the first time in an integrative approach, by the present invention. Thus, benefits provided by the present invention include gentle enzymatic tissue removal enhanced by mechanical "stripping" action of the locally directed protease stream, superior pain reduction and wound healing provided by inclusion of anesthetics, coagulants/anticoagulants and antibiotics in the protease solution and availability of removed skin cells for histological examination and/or cell culture from the treated lesions. In addition, control of temperature, ph and flow rate of the stream of protease solution, and provision for on-site activation of stabilized enzyme preparations ensure delivery of accurate, effective levels of catalytic activity, to the lesion surface.

Proteases are widely applied in the debridement of non-viable tissue, for example, as described by Mekkes, J. R. et al. (same as above); conditioning of skin imaged by $CO_2$ laser surgery, for example, as described by Gaspar, L. et al. (same as above); and aging, for example, as disclosed in U.S. Pat. No. 5,976,556 to Norton, et al., exploiting the ability of the enzyme to digest protein components of extracellular matrix without damaging healthy tissue The choice of suitable enzyme preparations, methods of application, and extent of treatment have emphasized the removal of debris and non-viable tissue. Since collagen, elastin, fibrinin and proteogly-can predominate in the skin's extracellular matrix, and are of even greater significance in abnormal conditions such as keloids, scars, warts and fibroses, enzymes of the type collagenase, elastase and hyaluronidase, and combinations thereof, have been most often employed for treatment of dermatological lesions. However, the methods of treatment with these enzymes have been limited to topical application and intradermal injection.

Thus, Pinnell, in U.S. Pat. No. 4,645,668, teaches the treatment and prevention of acne and hypertrophic scars, keloids, wrinkles and cellulite with repeated intradermal injections of proteases, principally collagenase, with additional hyaluronidase. The author achieved significant resolution of most of the lesions treated, indicating the efficacy of protease digestion of matrix tissue, and reported few, if any, negative effects. However, repeated intradermal injections, over a period of weeks, were required to achieve the desired effects. In addition to the discomfort and protracted character of such a treatment regimen, no retention of cells from the lesions is made possible, necessitating conventional, surgical biopsy methods prior to enzymatic treatment. Similarly, de Faire et al. in U.S. Pat. No. 5,958,406, teach the treatment of a variety of conditions associated with cell-adhesion related processes with multifunctional enzyme krill protease, comprising chymotrypsin, trypsin, elastase, collagenase and exo-peptidase activity. Treatment of dermal and internal lesions is addressed, by topical, parenteral, aerosol, systemic, intramuscular and intradermal delivery of the protease compositions. Intradermal injection of proteases is recommended for treatments of scar and keloid lesions. Thus, cell collection or retention from the treated area is not possible and, as in other dermatological enzyme treatment protocols, no control of protease activity after administration is afforded.

Topical application, or injection of proteases offers little control over the level of catalytic activity remaining in situ, with autoproteolytic and normal dermal lytic and acidic processes causing unpredictable degradation. Although many protocols for topical or intradermal delivery of proteases depend on individual, empirical results for determining duration of treatment, it has been suggested that topical treatment application of acid proteases, compatible with the normal pH of human skin, can ensure greater control over active enzyme dosage, as described in U.S. Pat. No. 5,976,556 to Norton et al. However, in the aforementioned invention, as with other topical protease applications, there remains no ongoing control of enzyme activity post treatment.

Thus, according to one aspect of the present invention, there is provided a method of treating skin lesions, the method includes removing devitalized tissue and cells from the wound bed of a skin lesion, the method effected by applying a stream of solution containing an effective amount of at least one protease, over, and in contact with, the wound bed. By combining enzymatic digestion of intracellular matrix proteins and mechanical disruption of the wound bed by a fluid force, devitalized cells and tissue are dislodged from the tissue and may be further removed from the lesion site. Application of the protease solution via streaming onto the lesion surface affords precise localization and control of magnitude and duration of enzymatic activity, through manipulation of enzyme concentrations, pH, temperature, hydrophobicity/hydrophilicity of the enzyme solutions, intensity of streaming, duration and site of contact with protease solution throughout treatment As described above, the apparatus of the present invention provides such diverse control of protease treatment through, for example mixer 12, thermoregulator 14, pump 18 and applicator 24.

As used herein, the term "protease" refers to any biologically active molecule, typically a polypeptide, possessing enzymatic peptide hydrolase activity, including endopeptidase and/or exopeptidase activity.

In one preferred embodiment of the present invention, the protease is, but not limited to, vibriolysin, krill protease, chymotrypsin, trypsin, collagenase, elastase, dipase, proteinase K, *Clostridium* multifunctional protease and *Bacillus subtillis* protease. These represent proteases commonly employed in therapeutic methods, have demonstrated low incidence of undesirable side effects, and are commercially available in pure, purified or genetically engineered form, for example, Esperase, Subtilisin A, Savinase, and Durazyme, available from Novo Nordisk Bioindustry Japan K.K.; Protease N "Amano", Protease S "Amano", available from Amano Pharmaceutical K.K.; Bioprase, available from Nagase Seikagaku Kogyo K.K.; and Purified Collagenase, available from Advance Biofactures, Lynbrook, N.Y. *Clostridium* multifunctional protease and krill protease are easily prepared by one skilled in the art, for example, as disclosed in U.S. Pat. No. 6,416,626 to Markert et al., and U.S. Pat. No. 5,958,406 to de Faire et al., respectively.

Other proteases which may be selected are papain, bromelain, plasminogen activator, plasmin, mast cell protease, lysosomal hydrolase, streptokinase, pepsin, and any or all fungal, bacterial, plant or animal proteases. The protease solution of the present invention may contain a single protease, or, preferably, a plurality of proteases. The protease solution may also contain one or more glycosaminoglycans degrading enzyme, such as, but not limited to, various lysosomal hydrolases which include certain endoglycosidases (heparanase and CTAP degrade heparan sulfate and to a lesser extent heparin, and hyaluronidase from sheep or bovine testes degrade hyaluronic acid and chondroitin sulfate), various exoglycosidases (e.g., β-glucoronidase), and sulfatases (iduronate sulfatase), generally acting in sequence to degrade the various glucosaminoglycans. Bacterial lyases such as heparinase I, II and III from Flavobacteriun heparinum cleave heparin-like molecules, chondroitinase ABC from *Proteus vulgaris*, AC from *Arthrobacter aurescens* or *Flavobacterium* heparin, B and C from *Flavobacterium* heparin degrade chondroitin sulfate.

Of even greater advantage, then, is the combination of additional topical, non-protease substances capable of reducing undesirable side effects. Schmitt et al. in U.S. Pat. No. 4,122,158, teaches the application of a biopolymer comprising protease, antibacterial, antibiotic and antifungal substances for the treatment and prevention of scarring and contamination in burn wounds Even the mild degrees of bleeding, pain and scarring potentially associated with enzymatic removal of cells from skin lesions can be alleviated by application of suitable substances simultaneously with the protease solution. The apparatus of the present invention is well suited for delivering solutions containing additional active substances compatible with the protease activity, through the inclusion of such substances in the solution within the reservoir(s) comprising the debriding solution.

In a further, preferred embodiment of the present invention, the protease solution contains at least one of a local anesthetic, a coagulant and an anticoagulant. In yet another embodiment, the protease solution further contains an effective amount of an antibiotic. The protease solution may further comprise a suitable pharmaceutical acceptable carrier.

As used herein, the phrase "local anesthetic" refers to any agent applied within a proscribed region (e.g., not systemically) effecting significant reduction or inhibition of activity of nonciceptive substances, receptors and/or neural pathways. Non-limiting examples of commonly used local anesthetic agents are cyclo-oxygenase inhibitors (e. g. ibuprofen, indomethacin and ketorolac), 5-hydroxytryptamine receptor antagonists (e.g. amytryptyline), bradykinine receptor antagonists and histamine receptor antagonists.

As used herein, the term "coagulant" is defined as any agent that promotes clotting, or coagulation of blood, which may be safety applied to a dermatological lesion. A non-limiting example of such a coagulant material comprising gelatin, thrombin and calcium is described in U.S. Pat. No. 6,045,570 to Epstein, et al. Likewise, the term "anti-coagulant" refers to any agent which retards, inhibits or prevents the clotting or coagulation of blood, which—may be safely applied to a dermatological lesion, such as heparins, coumarins or other agents possessing thrombolytic activity.

As used herein in the specification and in the claims section below, the phrase "pharmaceutically acceptable carrier" refers to a pharmaceutically acceptable material, composition or vehicle, such as a liquid filter, diluent, solvent or encapsulating material, involved in carrying or transporting a compound(s) of the present invention within or to the subject such that it can perform its intended function. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar, buffering agents, such as magnesium hydroxide and aluminum hydroxide; alginic acid; fruit acids, pyrogen-free water; isotonic saline; Ringer's solution; ethyl alcohol; phosphate buffer solutions; and other non-toxic compatible substances employed in pharmaceutical formulations.

As used herein, an "effective amount" of antibiotic is intended to include the amount of antibiotic sufficient to significantly prevent and inhibit at least 50%, preferably 75% and most preferably 100% of microbial growth within a dermatological lesion of the subject being treated, such effective amount determined by one skilled in the art.

Preconditioning of the dermatological lesion surface may provide superior efficiency of subsequent protease treatment. Normal epidermis consists of layers of dead squamous cells which provide an effective mechanical barrier protecting the underlying viable dermal layers. Yu et al (U.S. Pat. Nos. 4,105,783 and 4,363,815) describe removal of dead cells from the keratin-rich stratum corneum with keratinolytic, desquamifying agent such as low molecular weight hydroxy or keto acids, and their esters. Such exfoliation of the skin is also achieved by cosmetic preparations containing dermabrasives, emollients, detergents, astringents and skin softeners. Thus, in a yet further embodiment of the present invention the surface of the lesion is pretreated by streaming of cleansing, softening, astringent, exfoliating and or dermabrasive agents. Apparatus 80 is well suited for this application, requiring only the provision of a suitable pretreatment solution in first reservoir 10, second reservoir 34 or 38, third reservoir 36, reservoir or ampoule 44, first reservoir or ampoule 48, second reservoir 52, first reservoir or ampoule 60, and/or second reservoir or ampoule 64.

It will be appreciated, in the context of the present invention, that autolysis and loss of functional enzyme concentration from catalytically active preparations of proteases constitutes a significant disadvantage of therapeutic administration of enzymes in topical, injected and/or other compositions. Active shelf life of the protease is limited, and precise control of enzyme activity at the site of administration is virtually unattainable, once injection or topical application is completed. A number of inventions have proposed the storage of biologically active substances, including enzymes, in contact with substances or under conditions limiting their native activity, effectively inactivation and stabilization, until contacted with substantially adequate amount of activating substance, or conditions sufficient to restore biological activity. For example, Edens, et al (U.S. Pat. No. 6,117,433) teach the stabilization of biologically active substances, such as vitamins, enzymes and antibiotics in high concentrations by preparation in water activity lowering agents such as salts, polyols, sequestering agents such as EDTA, phyate or gluconate, or antioxidants such as sulphites, glutathione, cysteine or ascorbic acid. Crystallized compositions of biologically active substances, typically more stable than aqueous preparations, are mixed with viscosifying agents to retard precipitation and ensure homogeneity of the biologically active composition. The disclosure further describes a dispensing system for such stabilized formulations, activating the biologically active substance by dilution with an aqueous composition. Nakagawa et al. in U.S. Pat. No. 5,409,546 describes the stabilization of serine protease derived from bacteria belonging to genus *Bacillus* for contact lens cleanser composition by addition of polyols, and the specification of a defined range of temperatures (room temperature to about 58° C.) within which the enzyme retains catalytic activity. Rowan et al. in U.S. Pat. No. 5,106,621 teaches the restoration of catalytic activity of a plant cysteine protease for treatment of burn wounds by addition of cysteine for regeneration of thiol groups. None of the aforementioned examples, however, relate to the administration of proteases for treatment of living cells, nor provide for ongoing, precise control of the activation of catalytic activity at the site of application.

Thus, in an embodiment of the present invention, there is provided a method for treating skin lesion protease is activated shortly prior to streaming the solution containing the effective amount of the at least one protease, over, and in contact with, the treated skin portion. The method wherein the protease is activated may be effected by: (a) keeping the protease at a first temperature in which the protease is substantially catalytically inactive and heating and/or cooling the at least one protease to a second temperature in which the at least one protease is catalytically active; and/or (b) providing the protease in a powder form and mixing the powder with a solution in which the protease is catalytically active; and/or (c) providing the protease in a first solution in which the protease is substantially catalytically inactive and mixing the first solution with a second solution so as to achieve a mixed solution in which the protease is catalytically active. The second solution may differ from the first solution with respect to pH, ion concentration, free metal concentration, hydrophilicity and hydrophobicity. For example, FIG. 3 depicts enzymatic surgery apparatus 80 in fluid communication with thermoregulator 14, enabling filling of first reservoir 10 with protease solution at sub-optimal, stabilizing temperatures, restoring catalytic activity by raising the temperature of the protease solution only shortly prior to application at the lesion site. Typically, enzymes are substantially inactivated at temperatures below 10° C., preferably 4° C. Activation of enzyme catalytic activity may be accomplished by heating and/or cooling the protease solution to optimal temperature, typically in the range of 30 to 40° C., preferably 37° C.

As used herein, the term "hydrophilicity" refers to the polar nature of a solution or compound, indicating its tendency to be attracted to other solutions or compounds exhibiting significant dipole moments. Likewise, the term "hydrophobicity" refers to the non-polar nature of a compound or solution, indicating its tendency to be repelled by and immiscible in other compound or solutions exhibiting significant dipole moments.

As used herein, the term "inactivation" refers to the reversible or irreversible suppression or loss of catalytic activity, for example, inactivation rendering proteolytic enzymes incapable of catalyzing hydrolysis of peptide bonds.

In the context of the present invention, it will be appreciated that many enzymes are designated as acid, neutral or basic, according to the physiological environment to which they are adapted. For example, the digestive enzymes pepsin and chymotrypsin, catalytically active in the acidic environment of stomach, exhibit low (pH 3-5) pH optima. Enzymes active in the environment of the dermis will typically have pH optima closer to the milder, acid mantle of the skin (pH 5.5-6.5). Thus, autolysis of the protease of the present invention may be inhibited prior to application by maintaining the protease at a non-optimal pH, and mixing the enzyme solution with an activating solution effectively achieving optimal pH shortly prior to administration to the treated lesion. Thus, in one preferred embodiment of the present invention, as illustrated in FIGS. 5 and 8, inactive stabilized protease solutions in second reservoir 34 and/or first reservoir or ampoule 48 are prepared in non-optimal pH, and the activating solution of third reservoir 36 and/or second reservoir or ampoule 52 restores optimal pH for catalytic activity upon mixing shortly prior to administration to the treated lesion. Most preferably, a pH optimum for catalytic activity is chosen which approximates the mildly acidic normal pH of mammalian skin. Similarly, protease solutions may be inactivated and stabilized by chelation of catalytically critical metal ions such as $Ca^{++}$ or $Mg^{++}$, with EDTA, for example. Activation may be then achieved by providing a concentration of the critical metal ion in the activating solution sufficient to achieve effective and/or optimal metal ion concentrations after mixing. Alternatively, or additionally, proteases may be stabilized and inactivated by preparation in solutions of reduced water availability, as in high salt and polyol concentrations, for example. Restoration of catalytic activity, shortly prior to streaming of the protease solution at the site of treatment, is accomplished by sufficient aqueous dilution by the activating solution. In the context of the present invention, it should be noted that enzymes extracted from different species (i.e., marine, thermophilic, halophilic, euthermic, mammalian, cryophilic, etc.) often demonstrate widely variable and species specific optima of pH, temperature, metal prosthetic group and ion concentration, and polar interactions (hydrophobicity/hydrophilicity).

In one preferred embodiment of the present invention, protease is provided in a non-fluid, powder form, mixing with an activating solution shortly prior to application to achieve catalytic activity. The viability of dried enzyme preparations is well know in the art, and many proteases of excellent grades of purity are commercially available in lyophilized form, for example Proteinase K (Sigma-Aldrich, Israel), Clostridopeptidase A (Sigma-Aldrich) and Elastase (Fluka Chemical Company Inc.). However, powdered, lyophilized or granulated enzyme preparations are often difficult to disperse homogeneously in diluent solutions. Thus, in one preferred embodiment of the present invention, illustrated in FIG. 6, powdered or lyophilized protease preparation(s) are held in first reservoir 10, contacted and mixed to homogenieity with activating solution from second reservoir 38 in mixer 12 shortly prior to delivery at the treatment site. In another embodiment described in detail above and illustrated in FIG. 9, the powdered or lyophilized inactivated protease is provided in separate reservoir or ampoule 60 and is contacted with, and dispersed in, the activating solution, provided in reservoir or ampoule 64, by the action of mixing mechanism 56 shortly prior to delivery at the treatment site. Thus, the method of the present invention incorporates the advantages of stabilized, non-aqueous powdered or lyophilized protease preparations while avoiding the disadvantages of poor dispersal in diluents and imprecise control of enzyme active at delivery.

It will be appreciated, in the context of the present invention, that catalytic activity of enzymes may be modified by activators and inhibitors. One such mode of regulation of enzyme activity is reversible inhibition, effected by the interaction of substrate analogs or regulatory molecules which cause changes in substrate binding and/or enzyme kinetics, effectively reducing catalytic activity, for example, as described in "Enzymes", chapter 3, in Molecular Cell Biology (1986): Darnell, J, Lodish, H and Baltimore, D, eds., Scientific American Books, Inc. Since such reversible inhibition of enzyme activity is concentration dependent, restoration of catalytic activity is achieved by contacting the inhibited enzyme preparation with appropriate volumes of diluent devoid of inhibitors. Thus, in a further embodiment of the present invention, stabilization of the protease solution is effected by the inclusion of an effective amount of reversible enzyme inhibitor(s). Activation of the stabilized protease preparation is effected by dilution with adequate volumes of activating solution devoid of inhibitor/and or inhibitor activity.

Similarly, the device and methods of the present invention provide for precise and accurate control of termination of enzymatic activity at the site of treatment and in the collected cells. Inactivation of protease activity effected by manipulation any of the aforementioned methods (pH, ion concentration, free metal concentration, hydrophilicity/hydrophobicity, water availability and reversible inhibition) may be effected by following protease streaming with application of effective amounts of protease-free solution(s) containing, for example, metal chelators, buffers of non-optimal pH and reversible protease inhibitors.

In the context of the present invention, it will be appreciated that many dermatological lesions contain abnormal skin cells and intracellular matrix. For example, psoriatic plaques are caused by abnormal epithelial cell turnover, the collagen of keloids and hypertrophic scars is characterized by abnormal crosslinking, warts are the result of papovaviral infection of epidermal cells, and various types of often hyperpigmented, hyperplastic cells comprise the many types of nevi (moles), keratoses and lentigines. Whereas proteolytic disruption of the intracellular matrix with subsequent resorption of the non-viable tissue has been the objective of previous enzymatic methods, in the present invention the abnormal cells of dermatological lesions are removed, effecting a superior treatment of these skin conditions.

It will be appreciated that the combination of mechanical "stripping" and enzymatic action of a stream of protease solution on the skin surface is suitable for removal of skin cells and debris for esthetic purposes. Thus, in a further embodiment of the present invention, controlled streaming of a protease solution may be used to cosmetically treat esthetically undesirable portions of the skin surface.

The methods and device of the present invention may also be applied for the treatment and/or removal of cells from the surface of tissue within a patient, or of internal tissues temporarily exposed during surgical procedures. Markert et al. (U.S. Pat. No. 6,146,626) describe the harvesting of cells for tissue culture from internal organs including liver, spleen, heart and skeletal muscle, connective and nerve tissue, glandular tissue, endothelium and others effected by digestion with *Clostridium* collagenase and elastase enzymes. De Faire et al. (U.S. Pat. No. 5,958,406) describe the treatment and prevention of infection in internal organs and body cavities by the injection or application of preparations containing krill multifunctional protease activity.

According to a further aspect of the present invention there is provided a method of removing and collecting cells from a surface of a viable tissue, the method is effected by streaming a solution containing an effective amount of at least one protease, over, and in contact with, the surface, thereby removing cells from the surface of the viable tissue, and collecting the cells. In one preferred embodiment of this aspect of the present invention the streaming of protease solution is applied to the tissue surface via an open surgical incision.

In another, more preferred embodiment the device and method of the present invention are employed to provide protease irrigation, removal and/or sampling for biopsy of a tissue surface or surfaces via the abovementioned "push-pull" cannula in a closed, fiber optic-directed surgical procedure. Non-limiting examples of such procedures are arthroscopy, cystoseopy, endoscopy, cholecystoscopy, laparoscopy, colonoscopy, and myringoscopy.

As used herein, the term "treatment" includes the diminishment or alleviation of at least one symptom associated or caused by the disorder being treated. For example, treatment can be diminishment of several symptoms of a disorder or complete eradication of a disorder.

As detailed above, the applicator and apparatus of the invention may comprise a tank adapted to collected the fluid and cellular debris draining from the occluded lesion. The importance of collecting cells removed from dermatological lesions cannot be overstated. Treatment without determining accurate diagnosis may lead to unnecessary removal of lesions, often incur unnecessary scarring, recurrences, and financial hardships. Of particular importance is the determination of cells type(s) comprising nevi and keratoses, due to the widespread prevalence of these lesions in adults, and their potential for malignant transformation (Sosis, A., Benign Tumors of the Skin, in Skin Diseases: Diagnosis and Management in Clinical Practice (1982), Binnick, S. A. ed, Addison-Wesley Publishing Co., USA. 166-230). As mentioned above, previous methods of non-surgical treatment of skin lesions, such as laser surgery, electrosurgery and chemical or enzymatic ablation have not provided any means for obtaining cells from the lesions, necessitating the use of traditional surgical biopsy techniques for accurate diagnosis.

Figure 4:
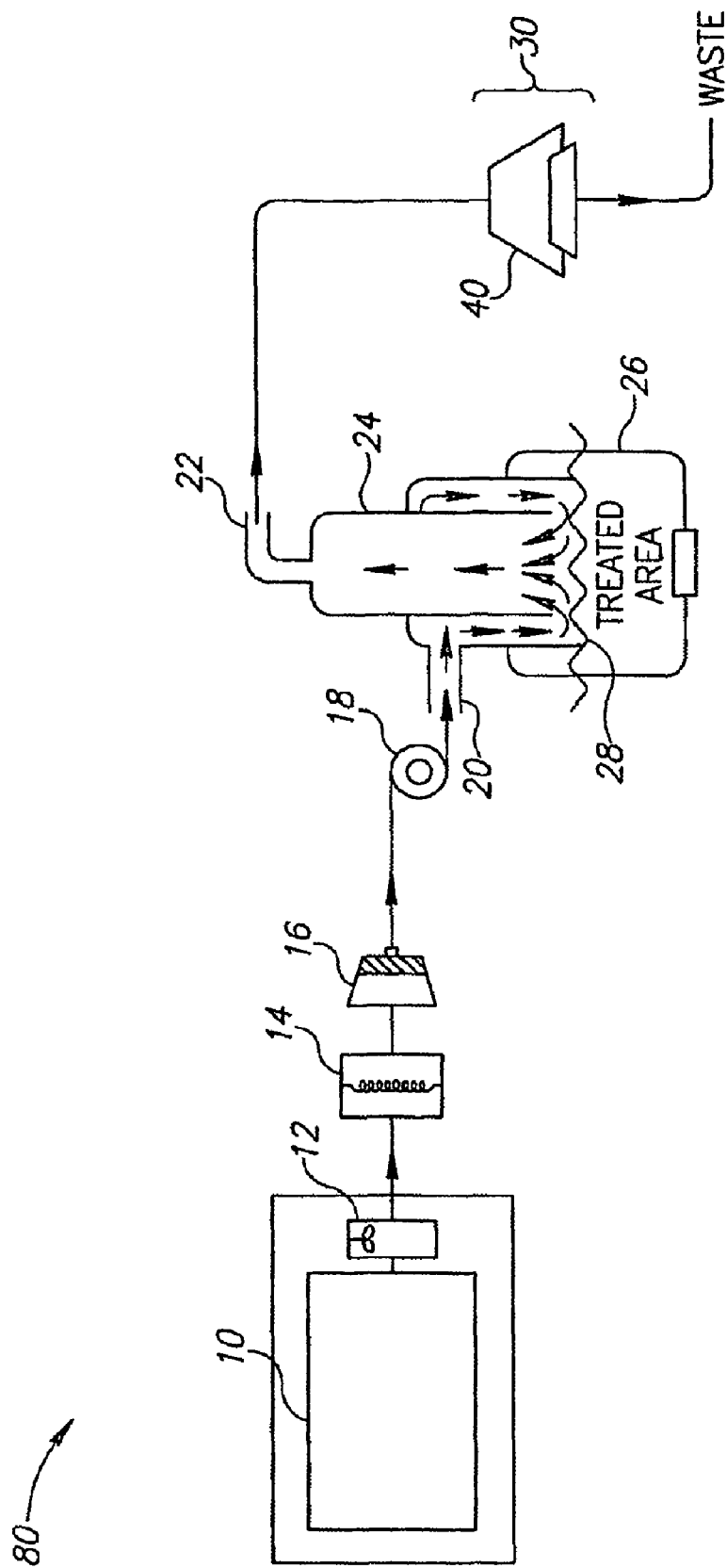
FIG. 4 is a cross-sectional view of a device in accordance with another embodiment of the present invention.

In the context of the present invention, it will be appreciated that confining the enzymatic activity to a stream of protease solution directed at the lesion surface, rather than topical application of creams or intradermal injection, provides the opportunity for retention of the cells removed from the treated lesion. Thus, the present invention provides a method of removing and collecting cells from a skin portion of a subject inflicted with a dermatological lesion, the method effected by streaming a solution containing an effective amount of at least one protease, over, and in contact with, the skin portion, thereby removing the cells from the skin portion of the subject; and collecting the cells. The products of protease digestion at the site of treatment are removed through the at least one outlet tube and are transferred to cell collector container, which is in fluid communication with the applicator. Separation of tie fluid and cellular components of the outflow of protease solution from applicator 24 may be accomplished by filtration, or, in another embodiment, by continuous flow centrifugation, as described above. Small volume continuous flow centrifuges, commonly used for separation of blood components (for example, the Ortho-PAT® System, Haemonetics Corporation, Braintree, Mass.) are commercially available and are easily adapted to the device of the present invention through fluid communication, as illustrated in FIG. 4. Alternatively, cell collection may be effected by retention on a column capable of adsorbing cells through interaction with proteinaceous, poly- and/or oligo saccharide or other cell-surface components.

Known cell separations involve several techniques, some of which are based on specific affinities. Other cell separation techniques rely on more serendipitous mechanisms such as entrapment of target cells in supports of various origins and structures. See, for example, Wigzell and Anderson, J. Exp. Med. 129:23-36, 1969; Rutishauser et al. Proc. Natl. Acad. Sci. 70, 1973; Wysocki and Sato, Proc. Natl. Acad. Sci. 75:2844-2848, 1978; Antoine et al. Immunochem. 15, 1987. See also, U.S. Pat. No. 6,008,040 to Datar. The basic process of affinity separation entails creating contact between cell mixtures to be separated and a support matrix to enable the target cells to preferentially attach, bind, adsorb or become trapped to and within the support, and then washing away the undesired cells, or vice-versa Specific affinity techniques use monoclonal antibodies to recognize specific markers on the membranes of cells and to "attract" the target cells to bind to the monoclonal antibodies. Specific affinity "attractions" of target cells also may occur by hydrophobic or hydrophilic interactions, metal-affinities, ion exchangers, and the like. Thus, in a further embodiment of the present invention, cell collection is effected by passage of the outflow stream from applicator 24 through cell collector 30 and contacting with a device, e.g. a cell-binding column, capable of retention of the cells and their separation from the outflow stream.

Additional objects, advantages, and novel features of the present invention will become apparent to one ordinarily skilled in the art upon examination of the following example, which is not intended to be limiting. Additionally, each of the various embodiments and aspects of the present invention as illustratively described hereinabove and as claimed in the claims section below finds experimental support in the following example.

EXAMPLES

Example 1

Enzymatic Debridement Using the Appartus and Methods of the Invention

Materials and Methods

The streaming system consisted of: a feeding reservoir, connecting inlet/outlet tubes, peristaltic pump (MP4 Minipulse 3, Gilson, France), a disposable applicator designed to direct the flow onto the treated site and a collecting vessel.

Animals and Tissue samples: The study was performed on groups of six 4-8 week-old [30-40 g body weight] male and female white mice, on groups of six mature (2-3 months old, 200-250 g body weight) Charles-River male rats, on adult male new-Zealand white (NZW) rabbit (3 kg body weight) and on pig skin samples. Mice and rats were anaesthetized with Avertin (0.1 ml of 1.25% tribromoethanol in saline per 10 g body weight; Sigma, USA) and the rabbit was sedated by ketamine rompun and anaesthetized with thiopenton sodium (Abbott Laboratories, Italy). The skin at the treatment area was shaved, animals were positioned on a jack and lifted until the applicator was tightened to the surface of the postetio-lateral aspect of the back of each animal. Fresh pig skin samples were removed from a white male (hybrid of large white with land race; 34 kg body weight), mounted on a plastic O-ring and fastened to the applicator.

Enzymes: All enzymes tested were lyophilized powders (Sigma-Aldrich Chemicals, USA). The enzymes were utilized as received without further purification. The following enzymes were used: Bromelain (B4882, dissolved in 0.01M Tris, pH 7.5); Collagenase (C01300, dissolved in 0.1M Tris, pH 7.6); Papain (P4762, dissolved in 0.01M Phosphate buffer, pH 6.5 containing 5 mM L-Cystein and 2 mM Ethyl-enediaminetetra-acetic acid (EDTA); Pepsin (P7012, dissolved in 10 mM HCl pH 2.9); Protease type X (Thermolysin, P1512 dissolved in 10 mM Sodium acetate (TA948368, Merck) and 5 mM Calcium acetate (C1000, Sigma) and Trypsin (T1005, dissolved in 0.01M Tris pH8.6).

Intact skin treatment: Freshly prepared solutions were continuously streamed onto confined shaved skin surface area of the anaesthetized mice, rat, rabbit or onto pig skin samples, at a flow rate of 5-6 ml/hour for 3 hours at room temperature, after which the animals were sacrificed and samples for histological examination were removed from treated areas.

Histology: Following the 3 hours treatment, the mice and rats were sacrificed with an overdose of chloral hydrate (Fluka chemicals, Switzerland) and rabbit was sacrificed with an overdose of thiopenton sodium. Full-thickness skin samples (4×15 mm) were removed for histological analysis from the margins of the confined area to allow comparison of treated and non-treated areas in same slide. Tissue samples were immediately fixed in 4% phosphate buffered formaldehyde solution for 48 hours, processed by routine histological procedures and embedded in paraffin. Serial sections perpendicular to the skin surface were cut at 8 μ thickness. The sections thus obtained were stained with hematoxylin and eosin for observations.

Experimental wound models: Thermal burns, 1-1.5 mm in depth, were induced after [10] by a direct contact of a tip of a standard soldering instrument for 30 sec on the posteriolateral dorsal shaved skin surface aspect of anaesthetized mice and rats. Freshly prepared proteases solutions, or their combinations, were applied by continuous streaming onto the wound within one hour from injury for 2-3 hours at the same flow rate as mentioned above. Full thickness linear fresh cuts were made by scalpel on the posterio-lateral aspect of animal back and immediately treated with continuous streaming of enzymes for 3 hours. Photographs of treated areas were taken immediately after treatment and after 7 and 20 days for assessment of the healing process.

Monitoring of streamed enzymatic activity: As proteolytic enzyme solution may loose its proteolytic activity due to autodigestion, residual activity of enymes employed was routinely monitored by in vitro biochemical assays recommended by the supplier, as follows:

1. Collagenase activity was assayed by the addition of 0.2 ml enzyme solution (1 mg/ml) into 3 ml of 0.25 mM Nα-Benzoyl-L-Arginine Ethyl Ester (B4500, Sigma) and 0.32 ml of 10 mM Dithioerythritol (D8255, Sigma) in 10 mM Tris buffer pH 7.5 containing 4 mM $CaCl_2$ (102382, Merck) and measuring $OD_{253}$ for 5 min. at room temperature.
2. Trypsin activity was assayed by the addition of 50 μl of enzyme solution [1 mg/ml] into one ml of substrate solution (5 mg of Nα-Benzoyl-DL-Arginine p-Nitroanilide (BAPNA, B4875, Sigma) dissolved in 0.5 ml of dimethylsulfoxide (DMSO, 102931, Merck) and added to 25 ml of Tris 10 mM pH 7.5. containing 4 mM $CaCl_2$) and measuring $OD_{405}$ for 5 minutes at room temperature.
3. Papain activity was assayed by the addition of 100 μl of enzyme solution (1 mg/ml) into 1 ml of BAPNA solution (prepared by dissolving 5 mg of BAPNA in 0.5 ml of DMSO and adding into 25 ml of 50 mM Phosphate buffer, pH 6.2 containing 5 mM Cysteine and 2 mM EDTA) and measuring $OD_{405}$ for 5 minutes at room temperature.
4. Bromelain activity was assayed by the addition of 50 μl of the enzyme solution (1 mg/ml) into 5 ml of 1% Casein solution (44016, BDH) in 50 mM Tris pH 8.5 in test tubes, equilibrated to 37° C. Following incubation for 10 minutes at 37° C. and pH 8-8.5, five ml of 10% Trichloroacetic acid (TCA, 33731, Riedel-de Haen) were added and the mixture incubated for additional 5 minutes at 37° C. The mixture thus obtained was centrifuged at 7,000 rpm for 10 minutes and $OD_{280}$ of the supernatant measured.
5. Thermolysin (Protease type X) activity was assayed as described above for Bromelain.
6. Pepsin activity assay: One ml of pepsin solution (0.01-0.05 mg/ml in 10 mM HCl) was added into 5 ml of 2% Hemoglobin solution (H2625, Sigma) in 10 mM HCl at 37° C. Following 10 minutes incubation, 10 ml of 5% TCA were added and the mixture incubated for additional 5 minutes at 37° C. The mixture thus obtained was centrifuged at 7,000 rpm for 10 minutes and $OD_{280}$ of the supernatant measured.

Results

Figure 13A:
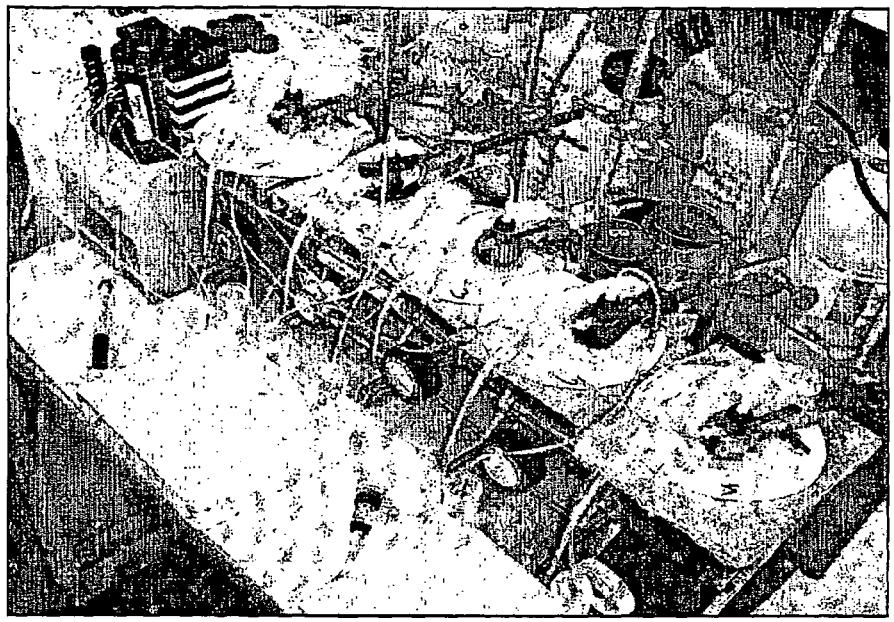
FIG. 13 exhibits experimental setups for simultaneous steaming of enzymatic solutions on treatment areas in six mice (A) and onto six separate areas on the same animal (B)
Figure 13B:
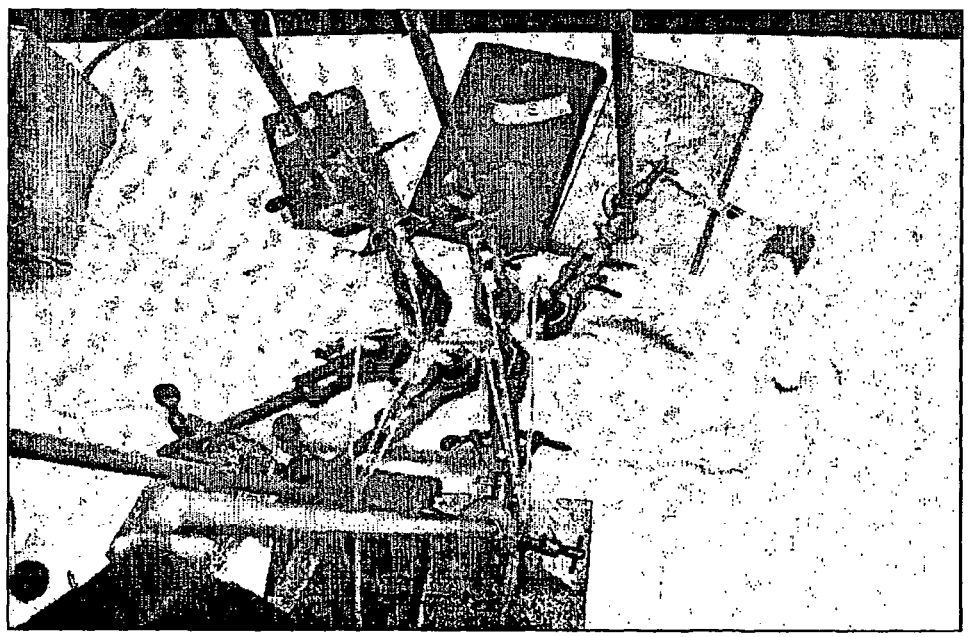
Figure 14A:
FIG. 14 shows histological sections of mice skin treated, for 3 hours, with a streaming solution devoid of proteolytic enzymes (A) and with streaming solutions comprising papain (B), trypsin and bromelain (C), trypsin (D) and pepsin (E)
Figure 14B:
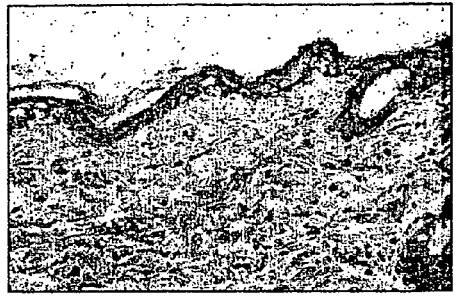
Figure 14C:
Figure 14D:
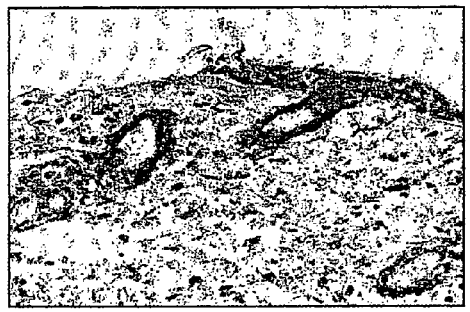
Figure 14E:

Effect of Enzyme Streaming on Intact Skin:

Controlled streaming of enzymes could be readily and conveniently applied as series of consecutive treatments using a multichanel pump, as demonstrated in FIG. 13A for treatments of six anaesthetized rats or treatment of six different sites on a larger animal (FIG. 13B). Effective digestion of different skin layers was readily achieved by streaming diluted buffered enzyme solutions for 3 hrs. The controlled streaming of 2 mg/ml papain onto mice affected digestion and removal of the outer keratinized layer (FIGS. 3A with 3B). Detachment of the epidermis from the dermis was effected by trypsin (4 mg/ml) and bromelain (5 mg/ml) mixture (FIG. 14C). Controlled streaming of 8 mg/ml trypsin solution effected complete digestion of the epidermis layer (FIG. 14D). Streaming of 3 mg/ml pepsin resulted in deeper penetration and collagen fibers digestion (FIG. 14E). Streaming of a mixture of 3 mg/ml collagenase and 1.5 mg/ml thermolysin resulted in digestion similar to the shown in FIG. 14D. Similar results were obtained by streaming of same solutions on rat, rabbit and pig skin.

Streaming of active enzyme solutions was essential to obtain these effects: streaming of buffer solution without enzymes was ineffective. Furthermore, streaming of enzyme solution for a few minutes to fill the system followed by flow arrest had no effect and visual change was not observed.

The specific activity of all streamed enzyme solutions remained stable (>85%) throughout the 3 hours application period. The minor loss of input activity was most probably caused by autodigestion.

Figure 15A:
FIG. 15 presents wounded skin sections before (A) and after application of a streaming solution comprising trypsin and collagenase (B)
Figure 15B:

Effect of Enzyme Streaming on Experimental Wounds:

Effective removal of fresh blood clots was readily achieved by streaming of trypsin and coflagenase mixture (3 mg/ml each) for 3 hrs onto freshly made cuts with smooth surface cleaning regardless of their shape (FIG. 15A-B).

Controlled enzymatic streaming for burn wound debridement was also readily achieved by 2 hours streaming of several proteases combinations: collagenase/thermolysin mixture (3 mg/ml and 1.5 mg/ml, respectively; FIG. 14B) trypsin/papain mixture (4 mg/ml and 2 mg/ml) or trypsin/collagenase mixture (3 mg/ml each).

Debridement with streamed enzymes e.g. papain or pepsin (2 mg/ml and 3 mg/ml, respectively, for 2 hours) resulted in smooth healing (compare FIG. 15A with FIG. 15B; photographs taken 20 days post burns induction).

Example 2

Enzymatic Removal of Epidermis

Using an apparatus including applicator 24 illustrated in FIG. 12, an enzyme solution containing Collagenase (1 mg/ml, Sigma Cat. No. C0130) and Thermolysin (0.5 mg/ml, Sigma type x, Cat No. P1512) in 0.1 M PBS buffer, pH 7.5, was applied onto a skin sample freshly removed from an adult female large-white pig (1 year old, 90 kg), mounted on a flat holder and pre-cleaned with 70% (v/v) aqueous ethanol, at a flow rate of 3-4 ml/hour for 3 hours at room temperature.

Following this treatment and detachment of the apparatus, complete hair removal from the treated area, accompanied by the formation of smooth, crater like removal of skin volume was macroscopically observed. The skin sample was immediately fixed in neutral buffered formalin (4% v/v) for 48 hours. The skin was then rinsed with distilled water, dehydrated in alcohol and embedded in paraffin. Stained histological serial sections (0.8 μm thick) were prepared in a plane parallel to the Epidermis-Dermis direction, mounted on slides, stained with Hematoxilin-Eosin and examined under light microscope. Examination of the edges of the treated area clearly indicated enzymatic epidermis removal from the treated area as compared to untreated skin.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the described embodiments. It is to be understood that the phraseology or terminology employed herein is for the purpose of description and not of limitation. The means, materials, and steps for carrying out various described functions may take a variety of alternative forms without departing from the invention.

What is claimed is:

1. An applicator for treating a skin lesion, comprising:
    (a) a housing unit having at least one aperture formed therein and a first longitudinal axis; and
    (b) means for affixing the applicator to the skin around the circumference of skin lesion; wherein the housing unit comprises:
        (i) a plurality of inlet tubes each capable of penetrating into the lesion at an adjustable depth and angle for delivering a therapeutic solution, each of said plurality of inlet tubes having a first longitudinal axis and comprising a first lumen for holding fluids and a second lumen configured to hold therein a deflectable wire extending along said first longitudinal axis and operatively linked thereto and enabling to maintain an angle and shape of each of said inlet tubes, whereas each of said plurality of inlet tubes is configured to be adjustable in position and in angle with respect to said housing unit and the skin lesion along its longitudinal axis through said at least one aperture; and
        (ii) at least one outlet tube for draining said therapeutic solution having a second longitudinal axis and configured to be adjustable along its longitudinal axis through said at least one aperture,
    the applicator being configured for providing a continuous flow of said therapeutic solution into a wound bed of the skin lesion.

2. The applicator according to claim 1, wherein the housing unit comprises a plurality of apertures, and wherein each of said plurality of inlet tubes and the at least one outlet tube extend through a corresponding one of each of said plurality of apertures, and further wherein each of said plurality of inlet tubes is adjustable in position and angle with respect to the housing unit.

3. The applicator according to claim 2, further comprising one or more sealing units, each sealing unit being configured to prevent the passage of fluids between the external diameter of an inlet tube or an outlet tube and its corresponding aperture.

4. The applicator according to claim 1, wherein each of said plurality of inlet tubes has a proximal end and a distal end, the distal end configured to face said skin lesion and wherein said distal end is smoothly curved to form a non-traumatic tip, with the opening at the distal end of at least one inlet tube is at an angle with respect to the central axis of the inlet tube.

5. The applicator according to claim 4, wherein distal end of at least one of said plurality of inlet tubes comprises a plurality of openings and each of said plurality of inlet tubes is constructed from a flexible elastomer of a silicone, polyurethane, natural rubber, neoprene or ethyl vinyl acetate.

6. The applicator according to claim 1, wherein at least one all of said plurality of inlet tubes is extendable or retractable along its respective longitudinal axis.

7. The applicator according to claim 1, further comprising at least one reservoir in fluid communication with the plurality of inlet tubes, the at least one reservoir is adapted for holding said therapeutic solution which comprises an effective amount of at least one catalytically active protease, wherein the at least one catalytically active protease is selected from the group consisting of: papain, bromelain, plasminogen activator, plasmin, mast cell protease, lysosomal hydrolase, streptokinase, pepsin, vibriolysin, krill protease, chymotrypsin, trypsin, collagenase, elastase, dipase, proteinase K, Clostridium multifunctional protease and Bacillus subtilis protease.

8. The applicator according to claim 7, further comprising (a) a connector being in fluid communication with at least one inlet tube of said plurality of inlet tubes and with the at least one reservoir, thereby to open and close the fluid communication between said at least one inlet tube and said at least one reservoir; (b) a separator being in fluid communication with at least one inlet tube of said plurality of inlet tubes and with the at least one reservoir, thereby to reversibly disconnect and reconnect said at least one inlet tube from said at least one reservoir; (c) control means in the form of a peristaltic pump or a drip counter and being in fluid communication with at least one inlet tube of said plurality of inlet tubes and with the at least one reservoir, or (d) a combination of (a), (b), and/or (c) to thereby control the flow rate of fluids flowing from the at least one reservoir through the at least one inlet tube.

9. The applicator according to claim 7, further comprising one of more of:
    a thermo-regulating means in communication with the at least one reservoir thereby to affect the temperature of fluids held in said at least one reservoir;
    at least one filter within at least one inlet tube of said plurality of inlet tubes, for filtering fluids flowing through said at least one inlet tube;
    a collecting reservoir being in fluid communication with the at least one outlet tube and configured to collect fluids draining from said at least one outlet tube; and
    a vacuum source being in fluid communication with the at least one outlet tube, adapted for generating a negative pressure at the occluded skin lesion.

10. The applicator according to claim 1, further comprising a plurality of reservoirs wherein a first reservoir of said plurality of reservoirs being adapted for holding a first solution comprising at least one catalytically non-active protease and wherein a second reservoir of said plurality of reservoirs being adapted for holding a second solution comprising an agent capable of activating the at least one catalytically non-active protease, the first reservoir and the second reservoir being in fluid communication with one another and at least one of said first and second reservoirs further being in fluid communication with at least one inlet tube of said plurality of inlet tubes.

11. The applicator according to claim 9, further comprising a mixing chamber that includes mixing means and being in fluid communication with said first and second reservoirs and with said at least one inlet tube, thereby to hold a catalytically active proteolytic mixture comprising said first and second solutions.

12. The applicator according to claim 1, wherein the means for affixing the applicator to the skin comprises a first plane attached to the housing and a second plane configured to surround and adhere to the lesion, wherein the second plane includes adhesive means that is biocompatible and is optionally covered with a protective detachable film.

13. The applicator according to claim 1, wherein said deflectable wire comprises a rigid material that is flexible and elastic and does not extend beyond said distal end of said at least one inlet.

14. An apparatus for treating a skin lesion, said apparatus comprising:

(a) a spacer for occluding an area comprising the skin lesion, the spacer having a lower plane facing the skin, an upper plane facing the housing, wherein the lower plane comprises adhesive means for affixing the spacer to the skin at the circumference of said skin lesion; and
(b) an applicator according to claim 1.

15. The apparatus according to claim 14, wherein the spacer comprises a resilient liquid-impermeable material of an elastomer or foam material selected from the group consisting of silicone, silicone foam, polyurethane, natural rubber, neoprene and ethyl vinyl acetate.

16. The apparatus according to claim 14, wherein the adhesive means comprises a material selected from the group consisting of: thermoplastic resin, pressure sensitive adhesive, hydrocolloid adhesive and rubber.

17. The apparatus according to claim 14, further comprising an adhesive plaster being in communication with said housing and extending outwards the first longitudinal axis of said housing, the plaster having an upper plane facing the applicator and a lower plane facing the lesion, wherein the lower plane comprises biocompatible adhesive means and is optionally covered with a protective detachable film.

18. A method for treating a skin lesion, the method comprising: (a) providing an applicator according to claim 1; (b) placing against the skin at the circumference of said skin lesion said affixing means, thereby affixing the apparatus to the skin at the circumference of said skin lesion to obtain an occluded lesion; (c) connecting the plurality of inlet tubes to at least one reservoir by a fluid communication, wherein the at least one reservoir encompassing a debriding solution comprising at least one catalytically active protease; (d) initiating a flow of the debriding solution from the at least one reservoir through at least one inlet tube of the plurality of inlet tubes to the occluded lesion; and (e) draining said solution from said occluded lesion through the at least one outlet tube.

19. The method according to claim 18, further comprising: (a) providing an apparatus comprising an applicator, said applicator comprising a housing unit having at least one aperture formed therein, and means for affixing the applicator, wherein said housing unit comprising : (i) a plurality of inlet tubes, each of said plurality of inlet tubes having a first longitudinal axis and configured to be adjustable along its longitudinal axis through said at least one aperture; and (ii) at least one outlet tube having a second longitudinal axis; (b) providing a spacer for occluding the skin lesion, the spacer having a lower plane facing the skin, an upper plane facing the housing of said applicator, wherein the lower plane comprises adhesive means for affixing the spacer to the skin at the circumference of said skin lesion; (c) affixing the lower plane of the spacer to the skin at the circumference of said skin lesion; (d) affixing the applicator to the upper plane of the spacer, thereby obtaining an occluded lesion; (e) connecting the plurality of inlet tubes to at least one reservoir by a fluid communication, wherein the at least one reservoir encompassing a debriding solution comprising at least one catalytically active protease; (f) initiating a flow of the debriding solution from the at least one reservoir through at least one inlet tube of the plurality of inlet tubes to the occluded lesion; and (g) draining said solution from said occluded lesion through the at least one outlet tube.

20. The method according to claim 18, wherein step (c) further comprises dispersing a sealing medium at the edge of the spacer that contacts the circumference of the occluded lesion.

21. The method according to claim 18, further comprising adjusting the position and angle of each of said plurality of inlets with respect to said housing unit.

22. The method according to claim 18, wherein connecting the plurality of inlet tubes to at least one reservoir by a fluid communication, provides a liquid-impermeable, vacuum-proof seal around the occluded lesion.

23. The method according to claim 18, further comprising providing control means being in fluid communication with at least one inlet tube of said plurality of inlet tubes and with the at least one reservoir, thereby initiating a controlled flow of fluids from the at least one reservoir through the at least one inlet tube, wherein the flow has a rate within the range of 1 ml/hour to 10 ml/hour.

24. The method according to claim 18, further comprising positioning the at least one reservoir on a higher level than the lesion, thereby initiating flow of debriding solution from the at least one reservoir through the plurality of inlet tubes to the lesion by gravitation.

25. The method according to claim 18, further comprising providing a plurality of control means, each control means being in fluid communication with a corresponding inlet tube of the plurality of inlet tubes and with the at least one reservoir, thereby controlling the flow rate within each inlet tube independently by a separate control means, wherein the flow rate within each inlet tube is within the range of 1 ml/hour to 10 ml/hour.

26. The method according to claim 18, further comprising providing at least one element being in fluid communication with the at least one reservoir and at least one inlet tube of the plurality of inlet tubes, the element is selected from the group consisting of: a control means adapted for controlling the rate of flow from the at least one reservoir to the at least one inlet tube; a connector adapted for opening and closing the fluid communication between the at least one reservoir and the at least one inlet tube; a filter for filtering a solution flowing within the at least one inlet tube; a mixing means for mixing the solution within the at least one reservoir; a thermo-regulating means for affecting the temperature of the solution within the at least one reservoir; a thermo-regulating means for affecting the temperature of the solution flowing within the at least one inlet tube; a separator being in fluid communication with at least one inlet tube of said plurality of inlet tubes and with the at least one reservoir, thereby to reversibly disconnect and reconnect said at least one inlet tube from said at least one reservoir; a vacuum source being in fluid communication with the at least one outlet tube, adapted for generating a negative pressure at the occluded skin lesion; and a collecting reservoir being in fluid communication with the at least one outlet tube configured to collect the fluids drained from the proximal end of said at least one outlet tube.

* * * * *